(12) United States Patent
Janik

(10) Patent No.: US 7,139,365 B1
(45) Date of Patent: Nov. 21, 2006

(54) X-RAY REFLECTIVITY SYSTEM WITH VARIABLE SPOT

(75) Inventor: Gary R. Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 156 days.

(21) Appl. No.: 11/025,472

(22) Filed: Dec. 28, 2004

(51) Int. Cl.
*G01N 23/20* (2006.01)

(52) U.S. Cl. ............................ 378/70; 378/84; 378/137

(58) Field of Classification Search ............ 378/70–90, 378/119, 121–138, 143, 145, 146
See application file for complete search history.

(56) References Cited

U.S. PATENT DOCUMENTS

| | | |
|---|---|---|
| 5,822,395 A | 10/1998 | Schardt et al. |
| 5,857,008 A | 1/1999 | Reinhold |
| 6,226,349 B1 | 5/2001 | Schuster et al. |
| 6,292,538 B1 | 9/2001 | Hell et al. |
| 6,771,735 B1 * | 8/2004 | Janik et al. .................. 378/70 |

* cited by examiner

*Primary Examiner*—Edward J. Glick
*Assistant Examiner*—Jurie Yun
(74) *Attorney, Agent, or Firm*—Bever, Hoffman & Harms, LLP; Jeanette S. Harms

(57) ABSTRACT

Thin film thickness measurement accuracy in x-ray reflectometry systems can be enhanced by minimizing scattering and beam spreading effects. A reflectometry system can include an x-ray tube that can produce an x-ray beam having any cross-sectional shape by scanning an electron beam in an appropriate pattern over a target in an x-ray tube. For example, the electron beam can be scanned over the target in a pattern having a non-unitary aspect ratio, so that the x-ray beam is generated from a source region having a non-unitary aspect ratio. The elongation allows the beam direction dimension to be substantially reduced, without causing overheating of the target. By blocking portions of the x-ray beam focused on the thin film and generating reflectivity curves in increments, the effects of scattering can be minimized.

21 Claims, 18 Drawing Sheets

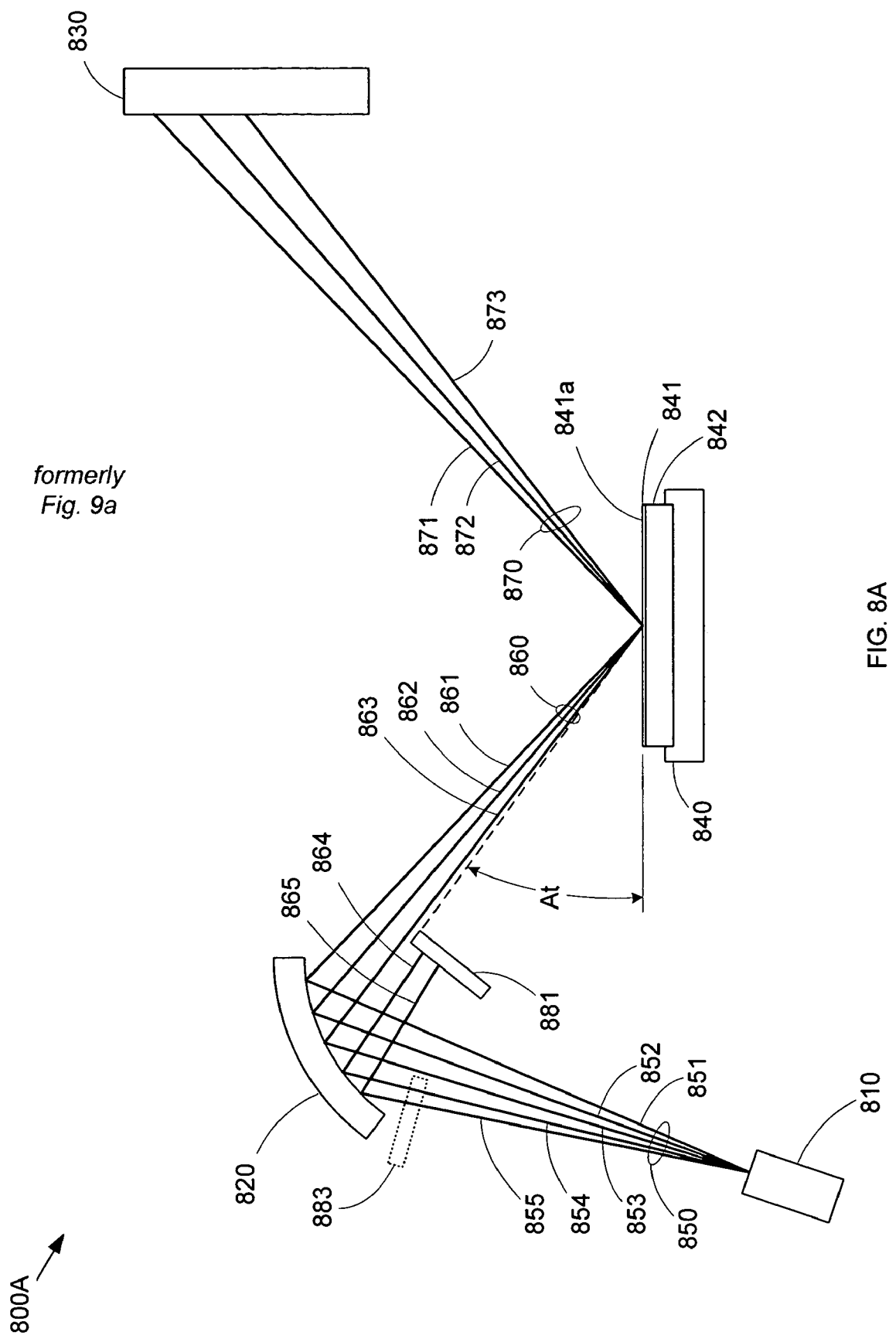

X-RAY REFLECTIVITY SYSTEM WITH VARIABLE SPOT

BACKGROUND OF THE INVENTION

1. Field of the Invention

The present invention relates to the area of non-destructive film thickness measurement. In particular, the present invention relates to a method and apparatus for improving the resolution and accuracy of x-ray reflectometry measurements of thin films.

2. Discussion of Related Art

Conventional thin film thickness measurement systems often use a technique known as x-ray reflectometry (XRR), which measures the interference patterns created by reflection of x-rays off a thin film. FIG. 1A shows a conventional x-ray reflectometry system 100, as described in U.S. Pat. No. 5,619,548, issued Apr. 8, 1997 to Koppel. X-ray reflectometry system 100 comprises an x-ray tube 110, an x-ray reflector 120, a detector 130, and a stage 140. A test sample 142 having a thin film layer 141 is held in place by stage 140 for the measurement process.

To measure the thickness of thin film layer 141, x-ray tube 110 directs a source x-ray beam 150 at x-ray reflector 120. Source x-ray beam 150 actually comprises a bundle of diverging x-rays, including x-rays 151, 152, and 153. X-ray reflector 120 reflects and focuses the diverging x-rays of x-ray beam 150 into a converging x-ray beam 160. Converging x-ray beam 160 includes x-rays 161, 162, and 163, which correspond to x-rays 151, 152, and 153, respectively. Typically, x-ray reflector 120 is a monochromator that ensures that only x-rays of a particular wavelength are included in converging x-ray beam 160.

Converging x-ray beam 160 is then reflected by thin film layer 141 as an output x-ray beam 170 onto detector 130. A detail view of this reflection is shown in FIG. 1B, with reflected x-rays 171, 172, and 173 corresponding to incident x-rays 161, 162, and 163, respectively. The x-rays undergo specular reflection, forcing angles A1, A2, and A3, of x-rays 161, 162, and 163, respectively, to be equal to angles A11, A22, and A33 of x-rays 171, 172, and 173, respectively.

As shown in FIG. 1C, the reflected x-rays are actually formed by reflections at both thin film surface 141a and thin film/substrate interface 142a. Using x-ray 162 as an example, the incident x-ray splits into a primary ray 172a and a secondary ray 172b at thin film layer 141. Primary ray 172a is reflected by thin film surface 141a at an angle A22. Secondary ray 172b is transmitted through thin film layer 141 and is reflected at thin film/substrate interface 142a, eventually exiting thin film surface 141a at angle A22.

Because both rays 172a and 172b exit thin film surface 141a at angle A22, the intensity of x-ray 172 is determined by the amount of constructive or destructive interference between the two rays. The two rays will be in phase if the difference between the optical path length of primary ray 172a and the optical path length of secondary ray 172b is equal to an integer multiple of the wavelength of x-ray 162. (Note that the optical path length of ray 172b includes the distance secondary ray 172b travels within thin film layer 141 multiplied by the index of refraction of thin film layer 141.) If rays 172a and 172b are in phase, the maximum intensity for x-ray 172 is achieved. However, if this optical path length difference is not an integer multiple of the wavelength of x-ray 162, then the two rays will be out of phase, thereby reducing the intensity of x-ray 172.

Note that the actual optical path length of secondary ray 172b within thin film layer 141 is controlled by the incident angle of x-ray 162. Therefore, the intensity of x-ray 172 is ultimately determined by incident angle A2. By simultaneously focusing a beam of x-rays spanning a range of incident angles at the thin film layer, a reflected beam of x-rays having varying intensities can be generated. Those varying intensities can be measured by sensor 130, as indicated in FIG. 1B. For example, reflected x-rays 171, 172, and 173 are shown impinging on a detector plane 130a of detector 130 at points 181, 182, and 183, respectively. Points 181, 182, and 183 typically comprise sensor pixels capable of measuring incident x-ray intensity. The known pixel positions allow detector 130 to correlate the intensities at points 181, 182, and 183 with incident angles A1, A2, and A3, respectively. By performing a similar correlation for all the pixels on detector surface 130a, a reflectivity curve can be derived for thin film layer 140. An example reflectivity curve is shown in FIG. 2. By measuring the fringes in the reflectivity curve, the thickness of thin film layer 140 can be determined, as described in U.S. Pat. No. 5,619,548.

However, accuracy of conventional x-ray reflectometry systems can be severely limited by problems associated with x-ray scattering and spreading at the thin film surface. For example, FIG. 3 shows a detail view of x-ray reflectometry system 100, with incident x-rays 164 and 165 being reflected by thin film layer 141. X-ray 164 has an incident angle A4 and is reflected at an angle A44 as x-ray 174. In accordance with the law of specular reflection, angle A4 is equal to angle A44. X-ray 165 has an incident angle A5, and theoretically would be reflected at an angle A55 as x-ray 175r, where angle A55 is equal to angle A5. Because angle A4 is different from angle A5, x-rays 174 and 175r would ideally impinge on detector surface 130a at points 184 and 185, respectively. However, scattering caused by imperfections in the surface of thin film layer 141 can result in a portion or all of the incident x-rays parallel to x-ray 165 scattering off as x-ray 175s. X-ray 175s leaves the surface of thin film layer 141 at an angle A5s (which is not equal to incident angle A5). If angle A5s happens to be equal to angle A44, both x-rays 175s and 174 will impinge on detector surface 130a at point 184, thereby corrupting the intensity measurements at both points 184 and 185. Scattering is most likely to occur for x-rays having incident angles near the "critical angle" where total external reflection takes place.

The accuracy of conventional x-ray reflectometry systems is further degraded by problems associated with x-ray beam spreading. For example, FIG. 4A depicts the interface between x-ray beam 160 and thin film layer 141 where an illuminated spot B (i.e., the spot formed by the intersection between thin film layer 141 and x-ray beam 160) is formed on thin film surface 141a. Compared to a cross-section A at the most tightly focused portion of x-ray beam 160, illuminated spot B is significantly elongated in the beam direction. FIG. 4B shows cross-section A of x-ray beam 160 overlaid onto illuminated spot B. Conventional x-ray tubes produce an approximately circular x-ray beam, as indicated in FIG. 4B. Accordingly, the height H1 and width W1 of cross-section A are the same (i.e., unitary aspect ratio). In contrast, illuminated spot B is significantly distorted as it spreads across thin film surface 141a, and so has a length L2 and a width W2 at its largest dimensions. In a direction perpendicular to the beam direction and parallel to thin film surface 141a (sometimes referred to as the "neutral axis"), width W2 of illuminated spot B is increased slightly from width W1 of beam cross-section A. However, along the beam direction, height H1 of beam cross-section A is translated into a significantly greater length L2 of illuminated spot B. This disparity in x-ray beam height and illuminated spot length increases as the incident angle of the incoming x-ray beam decreases, and so is particularly problematic for the grazing-angle x-ray beams required in x-ray reflectometry. For example, at an incident angle of 0.5 degree, the length of the illuminated spot is roughly 100 times greater than the diameter of the x-ray beam.

Because of this lengthening of the illuminated spot, the resolution of conventional x-ray reflectometry systems can be degraded in two main ways. First, the increased illuminated spot size increases the chances that irregularities in the surface of the thin film will lead to scattering of the incident x-rays. Second, the larger spot size can allow reflections of x-rays having different incident angles to impinge on the same point on the detector. For example, if an x-ray reflects from the thin film layer at a point farther from the detector surface than an x-ray having a larger angle of incidence, both reflected x-rays could converge at the same pixel on the detector surface, thereby improperly skewing the measured results. This "overlapping" reflection becomes progressively more prevalent as the spreading of the illuminated spot increases, and can ultimately prevent any measurement of the thin film layer thickness. Note that the increase in illuminated spot width does not present a problem since the key reflection and intensity measurements are all along the beam direction.

In addition, it is desirable in semiconductor manufacturing to measure in as small a region as possible. It is especially desirable to measure within the scribe line (i.e., the region between active integrated circuits), which is usually less than 100 µm wide. Furthermore, even within the scribe line, space is very valuable and so it is desirable to limit the length of the measurement spot within the scribe line. The scribe line may contain patterned regions used for other types of tests, and the x-ray reflectivity measurement is best done on an unpatterned region. It is therefore desirable that the measurement be made in as small a region as possible, ideally in a region less than 100 µm×100 µm.

Therefore, it is desirable to reduce the illuminated spot size at a measurement location in an x-ray reflectometry system. However, reducing the x-ray beam diameter in conventional x-ray tubes can be difficult. X-rays are produced by aiming a high-energy electron beam (e-beam) at a metal target. This electron bombardment causes the target atoms to emit x-rays, but also significantly heats the exposed portion of the target. Since the energy level of the electrons in the e-beam must remain at a specific level to cause the target atoms to emit the desired x-rays, reducing the cross-sectional area of the e-beam increases the energy flux at the exposed portion (source spot) of the target. This in turn increases the required rate of heat conduction away from the source spot to prevent overheating. Therefore, the minimum size of the e-beam is constrained by the thermal conductivity of the target material surrounding the perimeter of the source spot.

Accordingly, it is desirable to provide an x-ray reflectometry system that minimizes the effect of beam spreading at a measurement location while maintaining sufficient x-ray flux at the measurement location.

SUMMARY

Conventional x-ray tubes in x-ray reflectometry systems generate an x-ray beam that emanates from a target source spot having a unitary aspect ratio. Consequently, when such an x-ray beam is incident on a test sample at a low angle of incidence, the actual illuminated area on the test sample is much larger than the cross-sectional area of the focused x-ray beam, resulting in measurement inaccuracy or undesirable exposure of the sample measurement area. An x-ray beam from a non-unitary aspect ratio source region on a target can be generated by scanning an electron beam across the source region. The long dimension of the source region can be oriented perpendicular to the x-ray beam direction to minimize the effects of beam spreading at the measurement spot. Furthermore, by adjusting the scanning pattern and power of the electron beam, an x-ray beam having any desired characteristics can be quickly and conveniently generated.

In one embodiment, an x-ray reflectometry system can include an x-ray tube for generating an x-ray beam, beam focusing optics for focusing the x-ray bean onto to measurement location on a test sample, and a sensor for measuring x-rays reflected from the measurement location, with the x-ray tube including a target (anode), an electron source (cathode) for generating an e-beam, and a scanning mechanism for scanning the electron beam across a source region of the target to cause the source region to emit an x-ray beam. The source region can take any shape, and in one embodiment, the source region can have a non-unitary aspect ratio, with a long dimension of the source region being oriented substantially perpendicular to the direction of the x-ray beam. In one embodiment, the scanning mechanism can be a beam deflection element, while in another embodiment, the scanning mechanism can be a positioning mechanism for adjusting the relative position between the electron source and the target. In another embodiment, the x-ray tube can include a beam shaping element for modifying the cross-sectional shape of the e-beam before it is scanned across the source region. In another embodiment, the target can be tilted relative to the direction of the x-ray beam such that the aspect ratio of the resulting x-ray beam is greater than an aspect ratio of the source region. In one embodiment, the sensor can be a sensor array for measuring reflected x-ray intensity across a range of positions and then correlating those intensity measurements with angle of incidence to generate a reflectivity curve. In one embodiment, the x-ray reflectometry system can include an optional gate for blocking a portion of the x-ray beam directed at the test sample to allow more targeted intensity measurements, while an optional second gate can be included for blocking x-rays scattered by the first gate. In another embodiment, the sensor can be a single element detector for measuring total intensity of the reflected x-rays, while the x-ray tube can be configured to generate an x-ray beam with a relatively narrow cone to allow correlation of the total intensity measurement with a particular angle of incidence between the x-ray beam and the measurement location. In another embodiment, the x-ray reflectivity system can include a positional adjustment mechanism (such as a goniometer) for adjusting the angle of incidence between the x-ray bean and the measurement location.

In another embodiment, a method for taking an x-ray reflectometry measurement can involve generating a first x-ray beam by scanning a first e-beam across a first source region of a target to cause the first source region to emit the first x-ray beam, focusing the first x-ray beam into a measurement location on a test sample, and measuring a first set of x-rays reflected from the measurement location. In one embodiment, the first source region can have a non-unitary aspect ratio, with the long dimension of the first source region being substantially perpendicular to the direction of the x-ray beam. In another embodiment, measuring the first set of x-rays reflected from the measurement location can involve measuring an intensity at each of a set of detection locations on a sensor array, and correlating the intensity at each detection location with an angle of incidence to generate a reflectivity curve. In another embodiment, the method for taking the x-ray reflectometry measurement can further involve generating a second x-ray beam by scanning a second e-beam across a second source region of the target to cause the second source region to emit the second x-ray beam, focusing the second x-ray beam onto the measurement location on the test sample, and measuring a second set of x-rays reflected from the measurement location. In one embodiment, the second source region can have a different shape than the first source region. In another embodiment, measuring the first set of x-rays can involve measuring a first total intensity of the first set of x-rays and correlating the first total intensity with a first angle of incidence between the first x-ray beam and the measurement location, while measuring the second set of x-rays can involve measuring a second total intensity of the second set of x-rays and correlating the second total intensity with a second angle of incidence between the second x-ray beam and the measurement location. In another embodiment, the power of the second e-beam can be set higher than the power of the first e-beam when the second angle of incidence is greater than the first angle of incidence.

The invention will be more fully understood in view of the following description and drawings.

BRIEF DESCRIPTION OF THE DRAWINGS

FIGS. 8A, 8B, 8C, and 8D show various exemplary methods of operating the x-ray reflectometry system of FIG. 6A to minimize the effects of scattering.

DETAILED DESCRIPTION

Conventional x-ray tubes in x-ray reflectometry systems generate an x-ray beam that emanates from a target source spot having a unitary aspect ratio. Consequently, when such an x-ray beam is incident on a test sample at a low angle of incidence, the actual illuminated area on the test sample is much larger than the cross-sectional area of the focused x-ray beam, resulting in measurement inaccuracy and/or undesirable exposure of the sample measurement area. An x-ray beam from a non-unitary aspect ratio source region on a target can be generated by scanning an electron beam across the source region. The long dimension of the source region can be oriented perpendicular to the x-ray beam direction to minimize the effects of beam spreading at the measurement spot. Furthermore, by adjusting the scanning pattern and power of the electron beam, an x-ray beam having any desired characteristics can be quickly and conveniently generated.

Figure 5A:
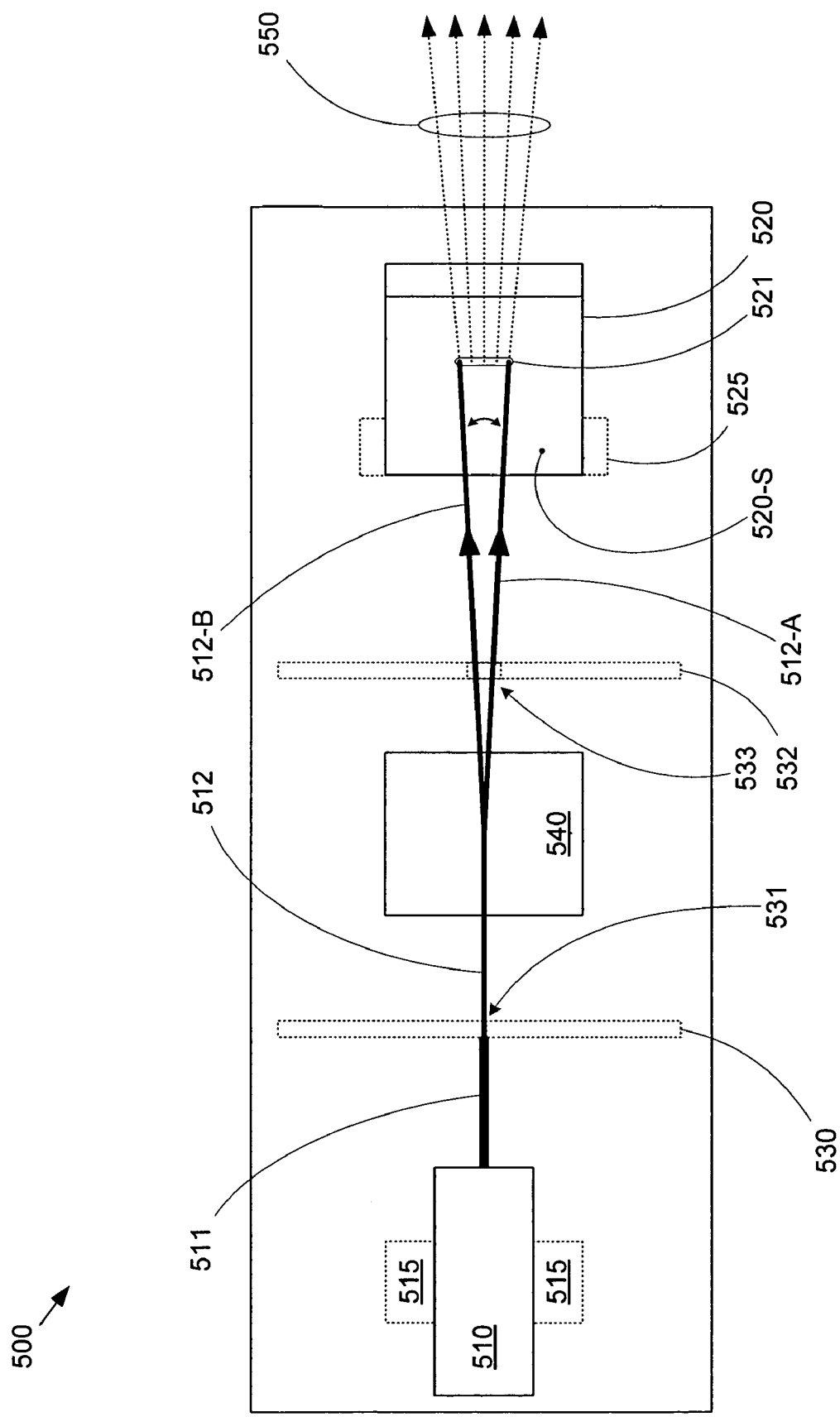
FIG. 5A shows an x-ray tube having beam shaping capabilities in accordance with an embodiment of the invention.

An embodiment of the present invention provides a system that includes an x-ray tube for producing a reduced-size x-ray beam, thereby enabling higher resolution measurement of thin films in an x-ray reflectometry system. FIG. 5A shows an embodiment of an x-ray tube 500 that can generate x-rays emanating from a target source region having a non-unitary aspect ratio. X-ray tube 500 comprises an electron source (cathode) 510, a target (anode) 520, an optional electron beam (e-beam) shaping element 530, an optional pattern shaping element 532, and a beam deflection module 540. Electron source 510 generates a source e-beam 511 that is directed at target 520. Optional e-beam shaping element 530 can be positioned between electron source 510 and beam deflection module 540 to manipulate the cross-sectional profile of e-beam 511 to generate an adjusted e-beam 512. Optional e-beam shaping element 530 can comprise any structure or system for modifying the shape of the cross-section of e-beam 511. For example, in one embodiment, e-beam shaping element 530 can be a plate that is substantially opaque to e-beam 511 except at an aperture 531 that allows a "shaped" portion of e-beam 511 to pass through as e-beam 512. In one embodiment, aperture 531 can have a substantially unitary aspect ratio (e.g., a circular aperture).

Figure 5B:
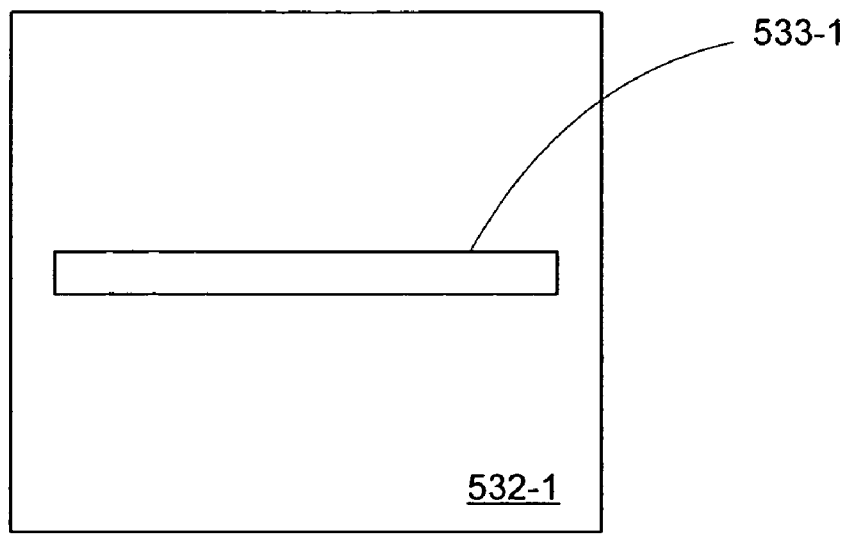
FIGS. 5B and 5C show exemplary e-beam shaping elements that can be used in the x-ray tube of FIG. 5A.
Figure 5C:
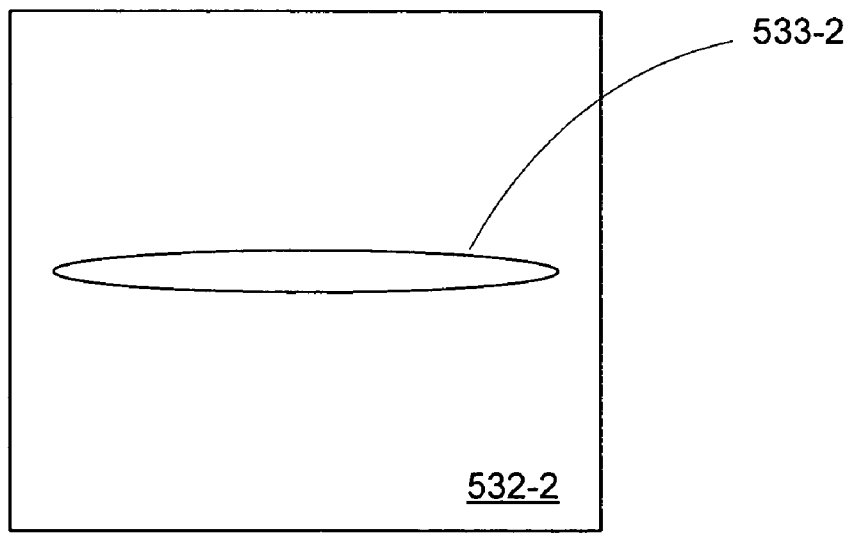

Meanwhile, optional pattern shaping element 532 can be positioned between beam deflection module and target 520 to provide additional control/accuracy over the portion of target 520 on which e-beam 512 is incident. Pattern shaping element 532 can comprise any structure or system for controlling the portion of target 520 scanned by e-beam 512. For example, in one embodiment, pattern shaping element 532 can be substantially opaque to e-beam 512 except at an aperture 533 that controls the portion of target 520 that can be exposed by e-beam 512. For example, FIGS. 5B and 5C show exemplary pattern shaping elements 532-1 and 532-2, respectively, that include apertures 533-1 and 533-2, respectively. Both apertures 533-1 and 533-2 are types of narrow slits that allow e-beam 512 to only scan across a relatively narrow portion of target 520. Other e-beam aperture configurations will be apparent to one of ordinary skill in the art. Note that pattern shaping elements 532-1 and 532-2 in FIGS. 5B and 5C, respectively, could also be used as e-beam shaping elements if a shaped e-beam with a non-unitary aspect ratio cross-section is desired. Note further that while apertures that provide e-beam/pattern shaping are described for exemplary purposes, various other implementations of optional e-beam shaping element 530 and optional pattern shaping element 532 (e.g., magnetic or electrostatic field generators) will be readily apparent.

Returning to FIG. 5A, beam deflection module 540 scans e-beam 512 (or e-beam 511 if e-beam shaping element 530 is not present) across a surface 520-S of target 520. Beam deflection module 540 can comprise any type of beam deflection mechanism, such as magnetic or electrostatic field generators. Note that e-beam 512 can be continuously on during the scanning process, or can be applied in discrete bursts (e.g., by turning electron source 510 on and off, by modulating the acceleration voltage of the e-beam or the voltage on e-beam control grids, or by placing and removing a shutter in the path of e-beam 512). The portions of target 520 on which e-beam 512 is incident during this scanning process define a source region 521 that emits an x-ray beam 550 that can subsequently be used in a metrology tool or any other x-ray-based device.

Figure 5D:
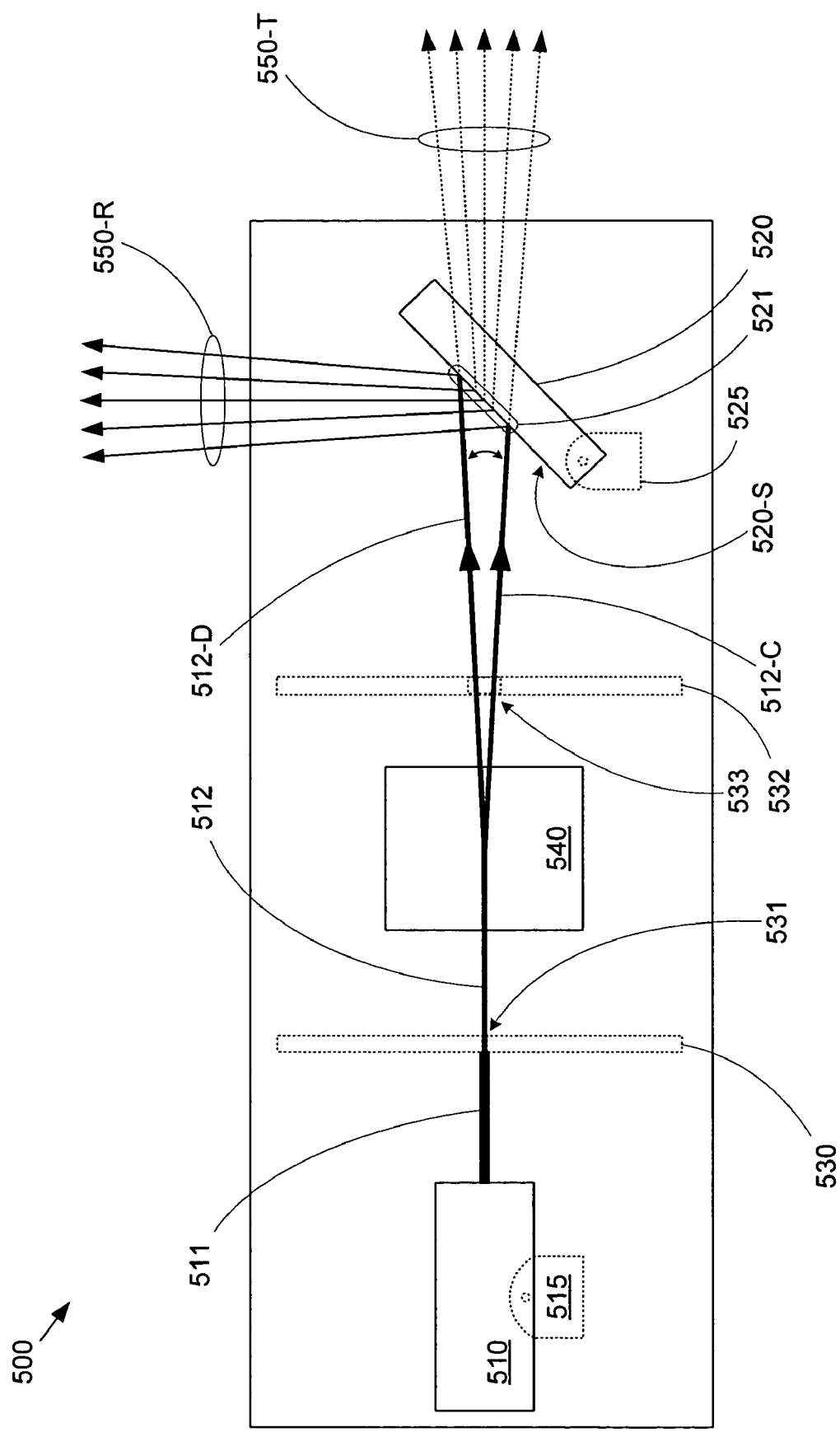
FIG. 5D shows a side view of the x-ray tube of FIG. 5A.

Note that because x-rays are emitted in all directions from source region 521, x-ray beam 550 can be selected to have any direction. For example, FIG. 5D shows a side view of x-ray tube 500 that depicts two possible x-ray beams 550-R and 550-T that can be generated via selection of the appropriate portion of x-rays emitted from source region 521. Note that as indicated in FIG. 5D, target 520 can be tilted (i.e., can be non-perpendicular to) x-ray beam 550-R or 550-T, thereby allowing the exposed region of target 520 to have a slightly smaller aspect ratio than the cross-section of x-ray beam 550-R (or 550-T), thereby "spreading out" the heated region of target 520. This in turn allows greater e-beam power to be applied to target 520, and consequently, enables generation of greater x-ray intensity. Generally, as the tilt of target 520 with respect to x-ray beam 550-R or 550-T (i.e., the closer target 520 gets to parallel with the outgoing x-ray beam 550) is increased, the thickness of target 520 should be decreased, thereby minimizing re-absorption of the emitted x-rays.

Note further that while for exemplary purposes the scanning of e-beam 512 across target 520 is described as being controlled by beam deflection module 540, any other type of scanning mechanism can be used that causes e-beam 512 to be scanned over source region 521 of target 520. For example, in one embodiment, electron source 510 and/or target 520 can include positioning mechanisms 515 and 525, respectively. Positioning mechanisms 515 and 525 can adjust the relative position between electron source 510 and target 520 to provide e-beam scanning capabilities. Various other e-beam scanning systems will be readily apparent.

Note further that in addition to controlling the direction of e-beam 512, in various other embodiments, beam deflection module 540 can include focusing optics for enhancing the sharpness of e-beam 512 as it is scanned across target 520. Note further that target 520 can have any construction that can generate x-ray beam 550-R and/or 550-T in response to an incoming e-beam 512. Note further that because x-rays will generally be emitted in all directions from target 520 in response to incident e-beam 512, in various embodiments, target 520 and/or x-ray tube 500 can include containment structures that only allow a portion of the x-rays emitted by target 520 to exit x-ray tube 500.

For exemplary purposes, the scanning of e-beam 512 across region 521 is indicated by a double-headed arrow between two e-beam positions 512-A and 512-B in FIG. 5A, and between e-beam positions 512-C and 512-D in FIG. 5D. Note that to generate a given x-ray beam 550, e-beam 512 could be scanned in just the direction indicated in FIG. 5A, in just the direction indicated in FIG. 5D, or in some combination of the two directions. Note further that e-beam 512 can be scanned across surface 520-S in any direction, thereby allowing source region 521 of target 520 to be defined with any size and shape. In one embodiment, beam deflection module 540 can control the scanning of e-beam 512 such that source region 521 has a non-unitary (i.e., having a long dimension and a short dimension) aspect ratio. In one embodiment, the long dimension of source region 521 can be substantially perpendicular to the direction of x-ray beam 550 in FIG. 5A, thereby allowing x-ray beam 550 to be focused back to the proportions of source region 521 at a target (measurement) location (as described in greater detail below with respect to FIGS. 6A–6C). Note that the "direction" of an x-ray beam as used herein refers to the central axis of the cone (or cylinder) of x-rays that make up the x-ray beam.

Figure 5E:
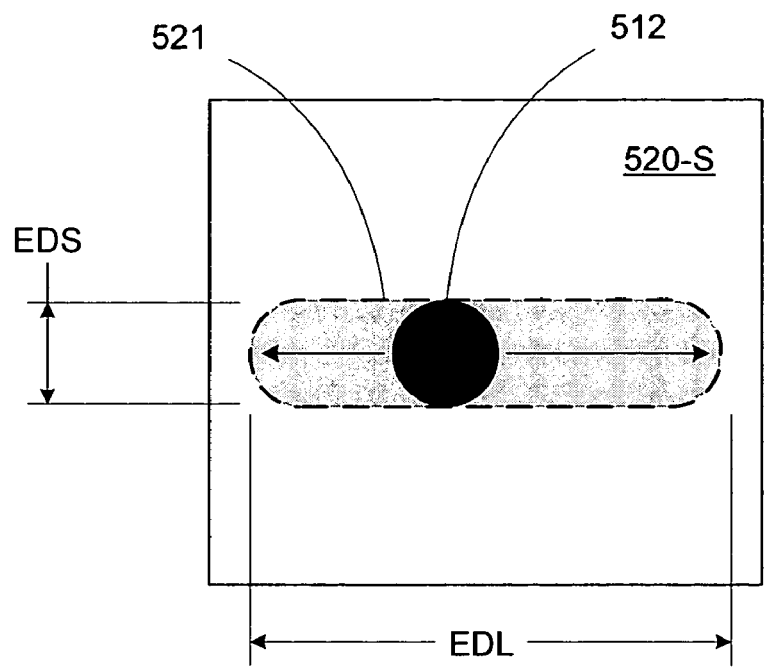
FIGS. 5E, 5F, and 5G show sample e-beam spot patterns that can be generated by the x-ray tube of FIG. 5A.

FIG. 5E shows a detail view of surface 520-S of target 520 in FIG. 5A, on which an exemplary source region 521 (shaded) is depicted. Scanning e-beam 521 across surface 520-S in the directions depicted by the arrows defines an oblong source region 521 having long dimension length EDL and a short dimension length EDS. Ideally, the scanning of e-beam 512 over source region 521 is performed fairly rapidly (e.g., 1 MHz or higher) so that the heat from the e-beam is not allowed to build up at any one spot and melt or damage the target material and so that the x-ray emission from source region 521 is relatively constant.

In this manner, source region 521 can effectively behave as a high aspect ratio x-ray source spot to reduce the effects of beam spreading at a measurement location (as described in greater detail below with respect to FIGS. 6A–6C). For example, in one embodiment, a 1 μm diameter e-beam 521 can be scanned back and forth in a line 40 μm in length at a frequency of 2 MHz, thereby defining the short dimension EDS (1 μm) and the long dimension EDL (40 μm) of source region 521.

Figure 5F:
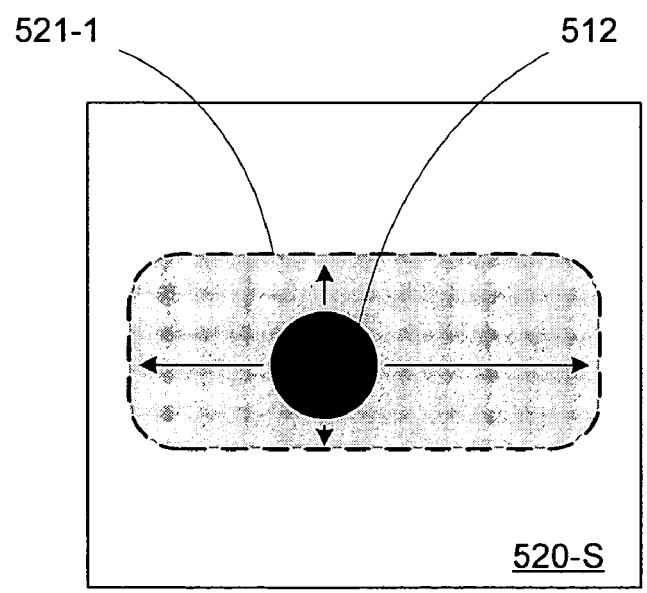

As mentioned above, e-beam 512 can be scanned across surface 520-S of target 520 in any direction. For example, FIG. 5F shows an exemplary source region 521-1 on target surface 520-S that can be formed by scanning e-beam 512 in the directions indicated by the arrows. Note that while only horizontal and vertical scan directions are indicated by the arrows for clarity, e-beam 512 can be scanned in any direction (e.g., diagonal or curvilinear patterns) over surface 520-S to provide coverage of source region 521-1. Because the scanning behavior of e-beam 512 over target surface 520-S can be easily changed (e.g., via a computer interface or other electronic control), the characteristics of the resulting x-ray beam (e.g., x-ray beam 550 in FIG. 5A) can be quickly changed by x-ray tube 500 shown in FIG. 5A.

Figure 5G:
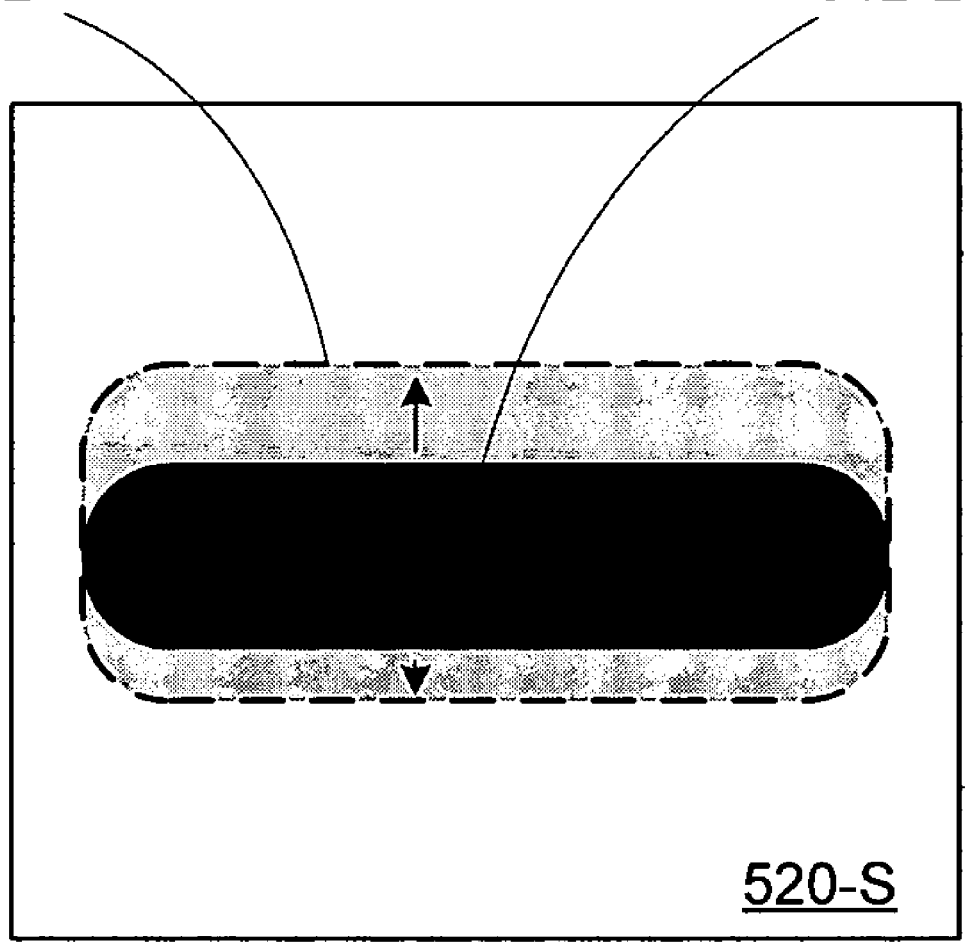

Note that while e-beam 512 is depicted as having a substantially circular cross-section in FIGS. 5E and 5F for exemplary purposes, e-beam 512 can have any cross-sectional shape. For example, FIG. 5G shows an exemplary source region 521-2 on target surface 520-S that can be formed by scanning e-beam 512-2 in the direction indicated by the arrows. E-beam 512-2 has an oblong cross-section that can, for example, be created by e-beam shaping element 530 in FIG. 5A. By scanning e-beam 512-2 in the directions shown, source region 521-2 can be created with a greater height than e-beam 512-2. Note that FIGS. 5E–5G are only exemplary, and various other embodiments can include any combinations of e-beam cross-sections and scanning patterns.

Figure 1A:
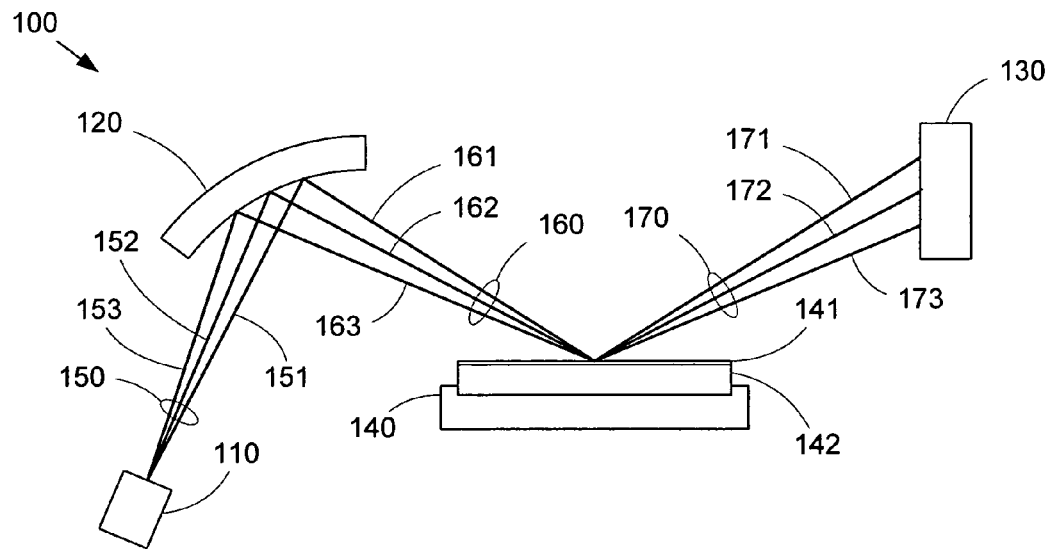
FIG. 1A shows a conventional x-ray reflectometry system.
Figure 6A:
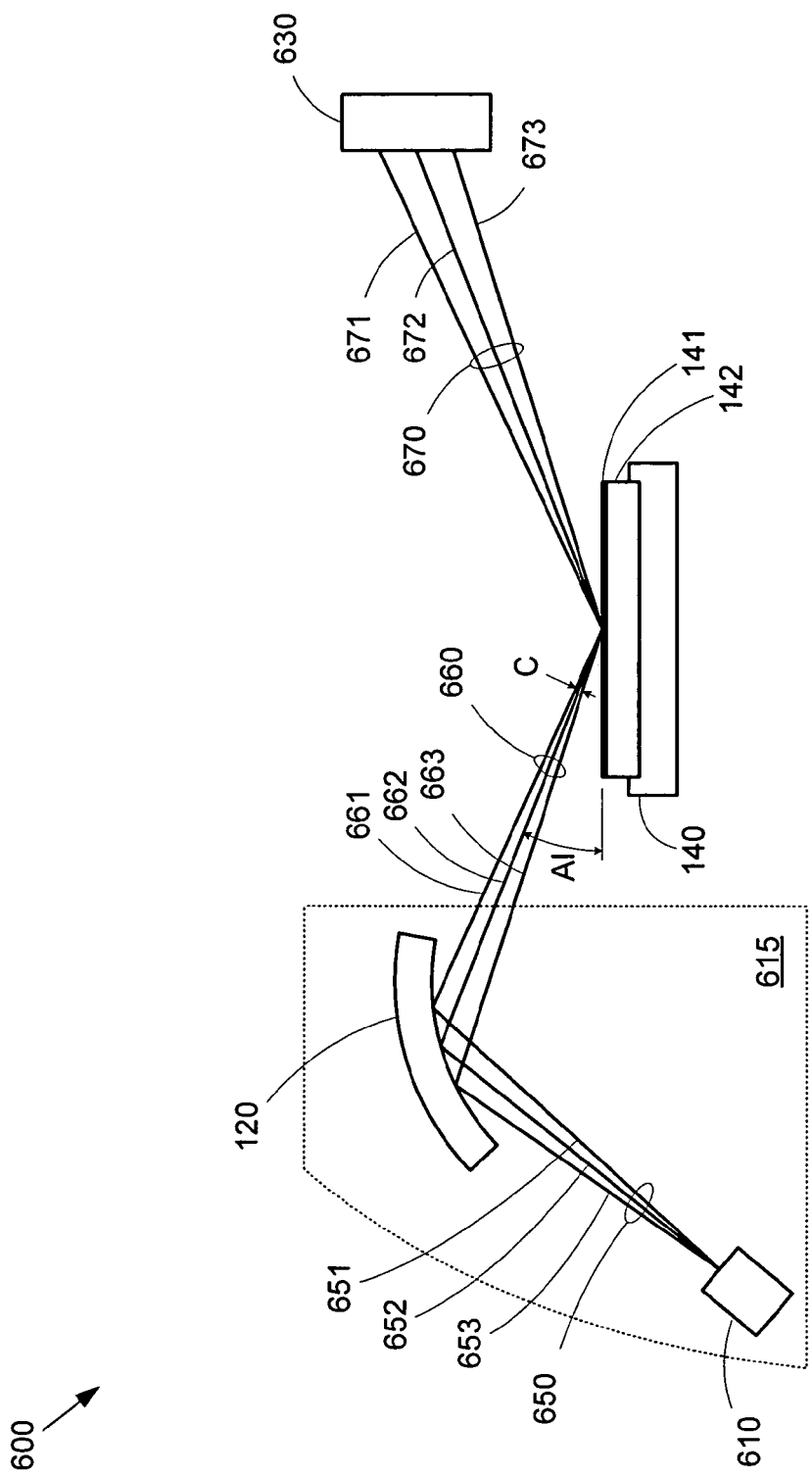
FIG. 6A shows an embodiment of an x-ray reflectometry system capable of providing reduced illuminated spot size.
Figure 6B:
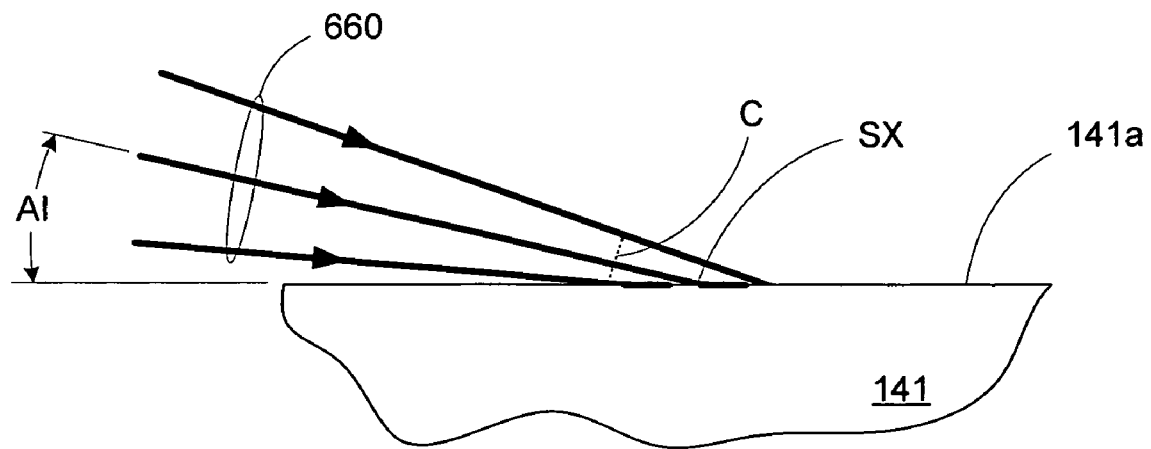
FIGS. 6B and 6C show exemplary details of x-ray beam spreading in the x-ray reflectometry system of FIG. 6A.

FIG. 6A shows an x-ray reflectometry system 600 that includes capabilities for adjusting the shape of an x-ray measurement spot formed on a thin film layer 141. X-ray reflectometry system 600 can be substantially similar to x-ray reflectometry system 100 shown in FIG. 1A, except conventional x-ray tube 110, which generates an x-ray beam by directing an e-beam at a static location on a target, is replaced with x-ray tube 610, which generates an x-ray beam 650 by scanning an e-beam over a portion of a target, as described with respect to FIGS. 5A–5F.

X-ray reflectometry system 600 operates in a manner substantially similar to that previously described with respect to x-ray reflectometry system 100. Source x-ray beam 650 is reflected and focused by x-ray reflector 120 as converging x-ray beam 660 onto thin film layer 141, and output x-ray beam 670 is measured by detector 630 to determine reflectivity data for thin film layer 141. In one embodiment, detector 630 can comprise an array detector, such as a photodiode array or multiwire gas chamber for spatially resolving output x-ray beam 670 to generate a reflectivity curve for thin film layer 141. In another embodiment, detector 630 can comprise one or more CCD detectors for measuring the intensity of output x-ray beam 670 across a range of output angles. Note that while depicted as a single element reflector for clarity, x-ray reflector 120 can comprise any type of beam focusing optics (e.g., a monochromatizing crystal, a graded multilayer reflector, a set of reflectors and optics) for directing, focusing (and optionally magnifying or demagnifying) source x-ray beam 650 onto thin film layer 141 as converging x-ray beam 660.

In one embodiment, x-ray tube 610 generates source x-ray beam 650 from a source region (e.g., source region 521 in FIG. 5A) having a non-unitary aspect ratio, with the long dimension of the source region being substantially perpendicular to the direction of source x-ray beam 650. A detail view of x-ray beam 660 striking thin film layer 141 is shown in FIG. 6A. X-ray beam 660 is focused to a minimum x-ray beam cross-section C, and forms an illuminated spot SX where thin film surface 141a intersects x-ray beam 660. As with conventional x-ray reflectometry systems, the area of illuminated spot SX is greater than cross-section C due to spreading at thin film surface 141a. However, the length (in the beam direction) of illuminated spot S is minimized by the small short dimension of x-ray beam cross-section C.

Figure 6C:
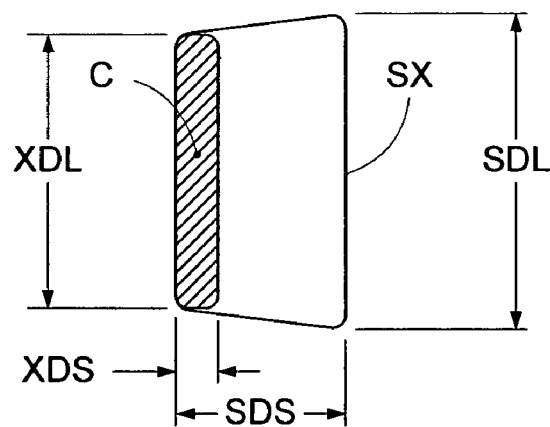

For example, FIG. 6C shows cross-section C overlaid on illuminated spot SX, according to an embodiment of the present invention. Cross-section C has a width (long dimension) XDL and a height (short dimension) XDS, with width XDL being significantly greater than height XDS. Typically, cross-section C will have proportions substantially similar to the proportions of the source region (e.g., source region 521) in x-ray tube 610. Although shown as having a substantially rectangular outline, cross-section C could have any outline with a non-unitary aspect ratio. Illuminated spot SX has a height SDS (in the beam direction) and a width SDL at its largest dimensions. As expected, while width SDL exhibits only a slight increase from the width XDL of x-ray beam cross-section C, the height SDS of illuminated spot SX in the beam direction is much greater than the short height XDS of x-ray beam cross-section C.

Despite this unavoidable elongation, the actual height SDS of illuminated spot SX is still greatly reduced compared to conventional x-ray reflectometry systems. Height XDS of x-ray beam 660 is substantially smaller than the cross-sectional height of x-ray beams in conventional x-ray reflectometry systems. Therefore, height SDS of illuminated spot SX is also significantly smaller than the height of the illuminated spot in those conventional x-ray reflectometry systems.

For example, the minimum (circular) source spot diameter of a conventional x-ray tube is limited to about 25 microns to prevent overheating of the target. At a 0.50 incident angle, the illuminated spot produced by such an x-ray tube will stretch out to a height of roughly 2.5 mm. In contrast, an x-ray tube that incorporates an electron beam that can be scanned over a target (e.g., x-ray tube 500 in FIG. 5A) can produce similar x-ray output from a 1 micron by 25 micron rectangular source region, due to the enhanced heat conduction capability provided by the high perimeter to area ratio of the source region on the target. The resulting narrow illuminated spot will thus only stretch to about 100 microns on the thin film surface, thereby providing an order of magnitude higher resolution over the conventional x-ray tube. In general, substantial benefits (e.g., increased x-ray intensity, reduced illuminated spot size) can be achieved if the aspect ratio of the source region is at least five (i.e., long dimension is at least five times the short dimension), although smaller aspect ratios can still provide improvements over x-ray beams generated using conventional unitary aspect-ratio source sports.

Figure 1B:
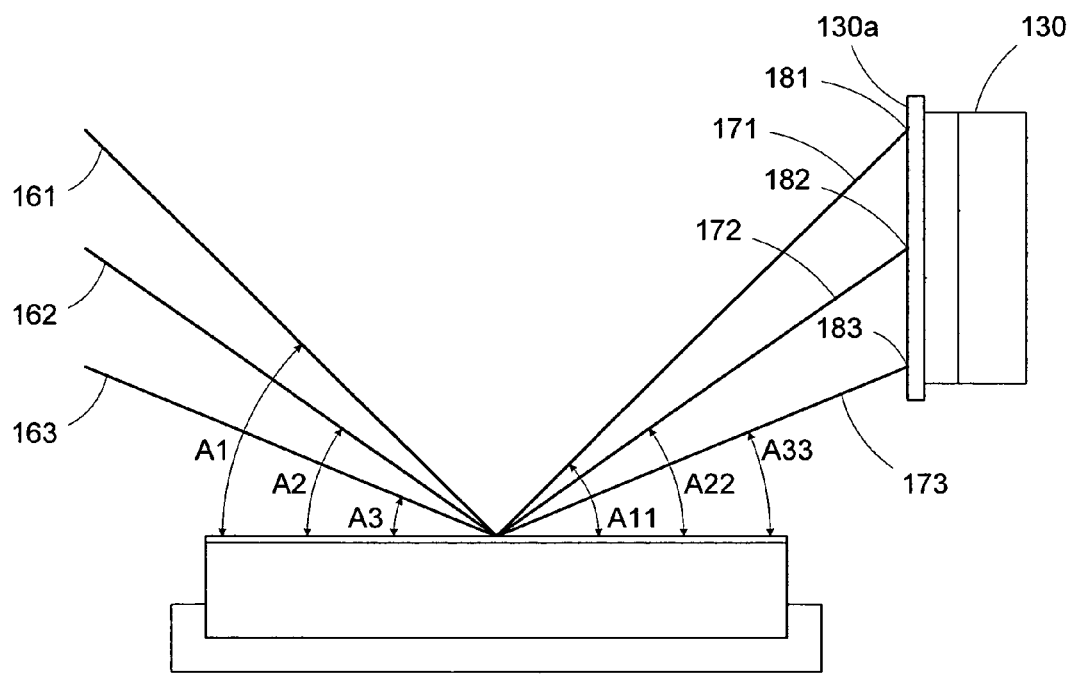
FIG. 1B shows a detail view of x-ray reflections onto a detector in a conventional x-ray reflectometry system.
Figure 1C:
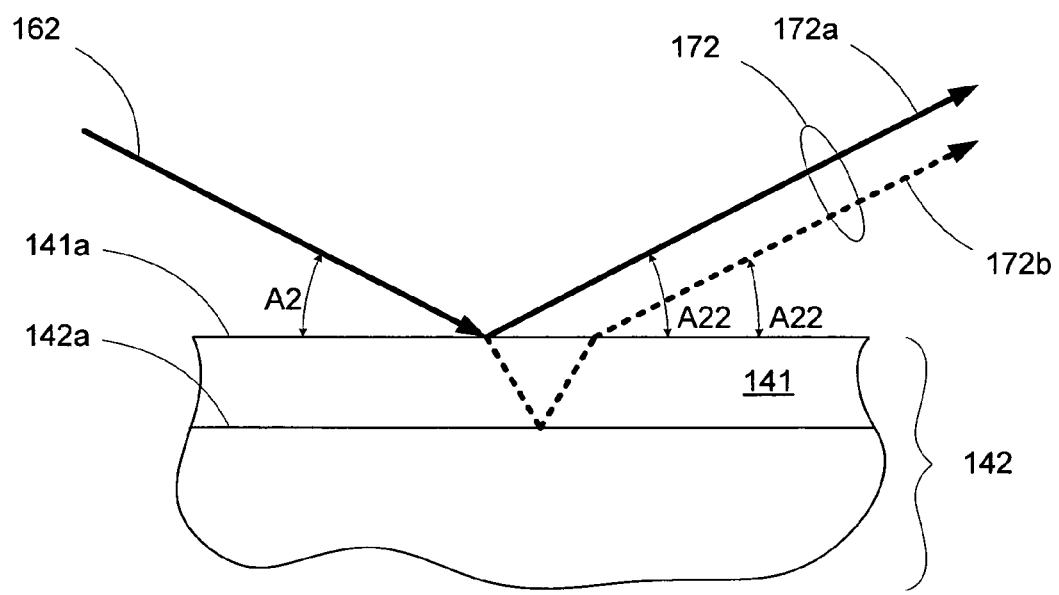
FIG. 1C shows a detail view of x-ray beam reflection at the surface of a thin film layer.
Figure 2:
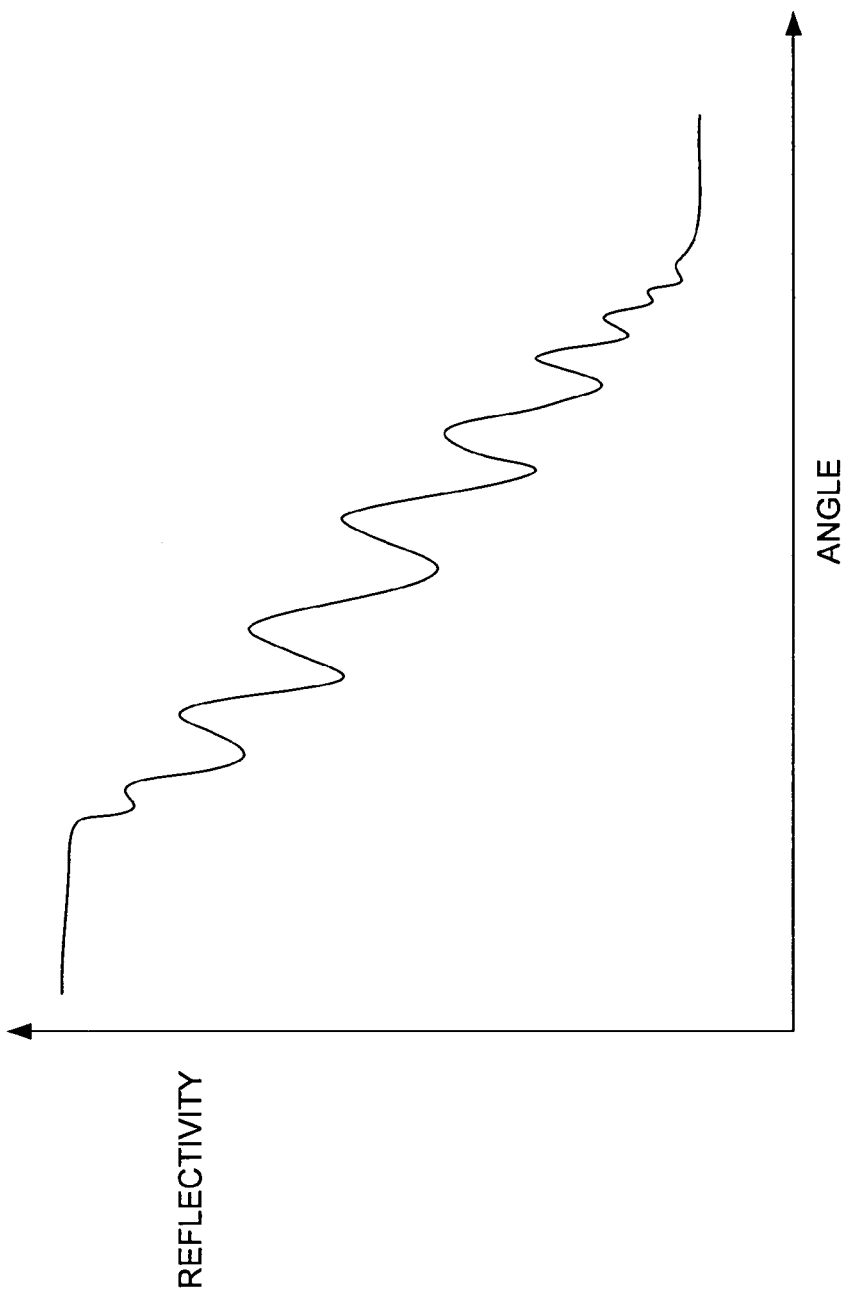
FIG. 2 shows an example of a reflectivity curve.
Figure 3:
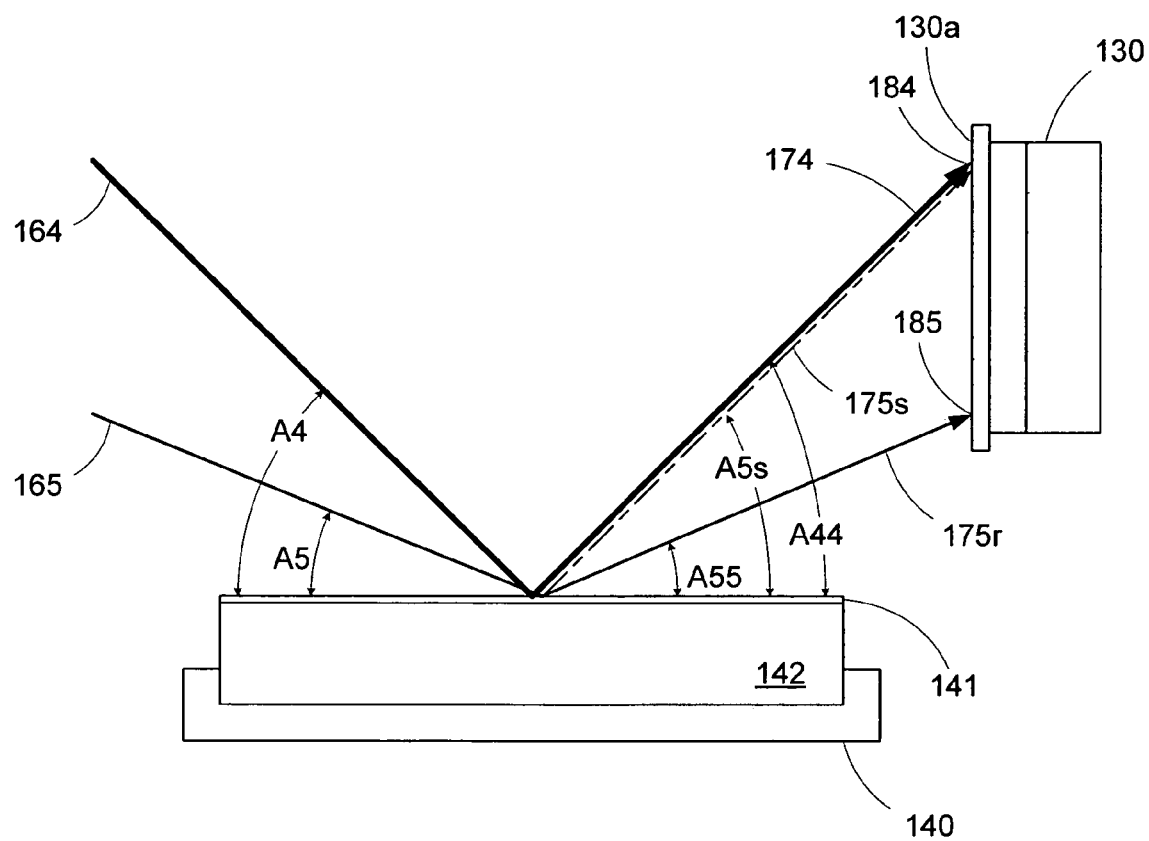
FIG. 3 shows an example of scattering in an x-ray reflectometry system.
Figure 4A:
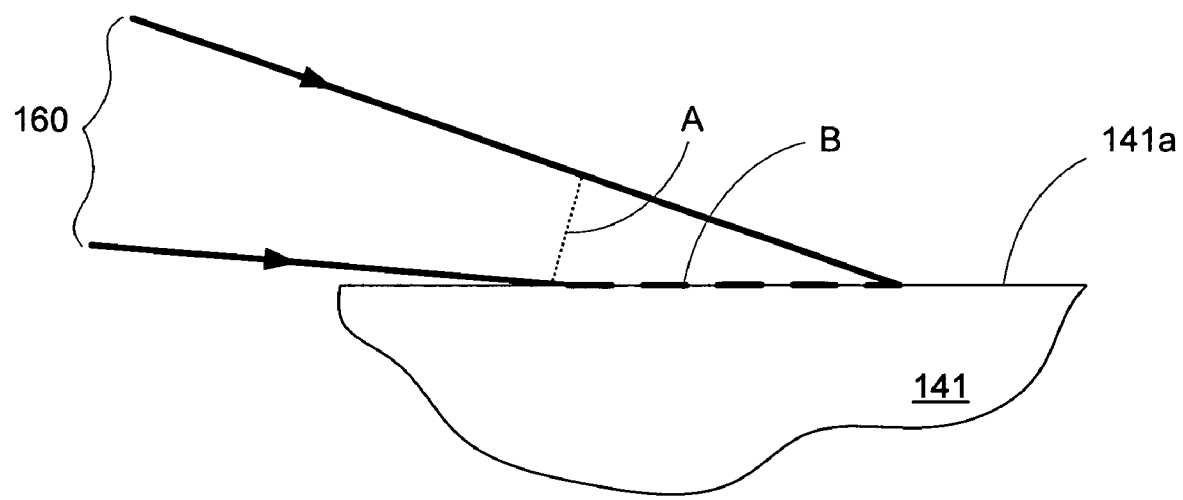
FIGS. 4A and 4B show details of x-ray beam spreading in a conventional x-ray reflectometry system.
Figure 4B:
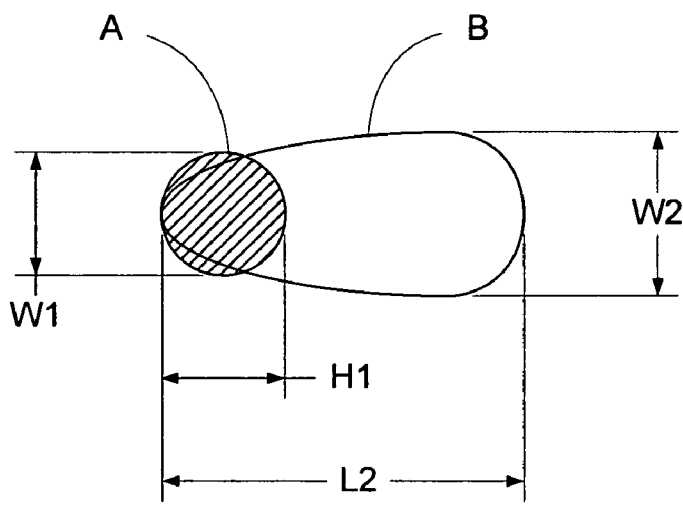

Returning to FIG. 6A, as noted above, x-ray reflectometry system 600 can perform reflectometry across a wide range of x-ray incident angles. Specifically, x-ray beam 660 includes individual x-rays that span a wide range of incident angles with thin film layer 141 (e.g., x-rays 661, 662, and 663 span a wide range of incident angles), and the resulting x-rays (e.g., x-rays 671, 672, and 673) are simultaneously measured at a multitude of detection locations (e.g., pixels) on sensor 630 (e.g., a sensor array such as detector 130 described in FIG. 1B). Each of the detection locations corresponds to an x-ray incident angle, which allows the intensity data to be correlated with incident angle to generate a reflectivity curve (such as shown in FIG. 2). In one embodiment, the total range of incident angles can be limited to about 3 degrees to provide a high-quality measurement of thin film layer 141.

However, in another embodiment, one or more measurements can be made using an incident x-ray beam 660 that includes x-rays that span a smaller range of incident angles with respect to thin film layer 141 (e.g., x-rays 661, 662, and 663 all roughly exhibit (e.g., are within 0.5° of) an angle of incidence AI with thin film layer 141). In one embodiment, such an x-ray beam 660 can be the result of x-ray tube 610 generating source x-ray beam 650 whose cone has been limited by an aperture either within the tube or external to it (i.e., individual x-rays in source x-ray beam 650, such as x-rays 651, 652, and 653, are all within 0.50 of the central axis of the cone). In one embodiment, the cone of x-rays for x-ray beam 650 can be limited to a small range of angles by an aperture within, or external to, x-ray tube 610. Alternatively, the cone can be limited by the size or design of the x-ray reflector, such that x-rays outside the desired cone do not reflect down to the sample. Various other methods of generating this limited-angular range x-ray beam 650 will be readily apparent.

To properly analyze thin film 141, a larger range of incident angles than is included in the limited-angular range x-ray beam 650 may be required. In such a case, the central angle of the cone of x-ray beam 650 can be changed by either discrete stepping or continuous scanning so that multiple measurements can be taken. Ideally, during such scanning, x-ray source 610 and x-ray reflector 120 would be adjusted such that the position of the illuminated (measurement) spot on test sample 142 does not move by a large amount for the different cone angles of x-ray beam 650. In one embodiment, small motions of the illuminated spot can be accommodated by moving test sample 142 via stage 140 so as to always maintain the illuminated spot at the same position on test sample 142 and at the correct focal position. Position sensitive detector 630 can then be used to record a reflected x-ray intensity for each of the incident angles contained within the cone of x-ray beam 660.

In one embodiment, position sensitive detector 630 can be moved in a vertical direction as the angle of incidence for x-ray beam 660 changes, so as to always intersect the entire cone of reflected x-ray beam 670. Alternatively, detector 630 can remain stationary if it is large enough to intercept all the x-rays in reflected x-ray beam 670 for all of the incident angles of x-ray beam 660. In any case, by taking a series of such measurements for multiple x-ray beams 660 that exhibit different angles of incidence with thin film layer 141, a set of angles of incidence versus x-ray intensity data points can be compiled (e.g., points on the reflectometry curve shown in FIG. 2).

This type of "stepped" reflectometry operation can be performed using an optional position adjustment mechanism 615 in reflectometry system 600. Position adjustment mechanism 615 can comprise any system (e.g., goniometer or computer numerical control (CNC) system) for adjusting the angle of incidence AI of x-ray beam 660 relative to thin film layer 141. In one embodiment, position adjustment mechanism 615 can include control logic for generating an x-ray beam from an appropriate source region using an appropriate e-beam power based on measurement conditions (e.g., angle of incidence and the composition of thin film 141). Then, as shown in FIG. 7A, position adjustment mechanism 615 can be used to change the angle of incidence AI between x-ray beam 660-1 and thin film layer 141 to a new angle of incidence AI-1 (previous positions of x-ray tube 610 and reflector 120 indicated by dotted outlines).

In another embodiment of the invention the range of incidence angles within the cone of x-rays is made extremely narrow (e.g., less than 0.1 degrees). The angle of incidence AI for the overall x-ray beam 660 can then be defined as the angle between thin film layer 141 (at the measurement location) and the central axis of the cone formed by the x-rays in x-ray beam 660 (which is essentially the average angle of incidence for the x-rays in x-ray beam 660), even though the individual x-rays in x-ray beam 660 may actually exhibit a small range of incident angles with thin film layer 141). Thus, each measurement taken by sensor 630 (which, in this case, would be a single element detector for measuring total (non-positional) intensity) represents an intensity correlated with a particular angle of incidence. The single element detector can be moved vertically as the angle of incidence is scanned, or it can be made large enough to intercept the x-rays at all incidence angles.

Note that because source x-ray beam 650-1 is generated within x-ray tube 610 by an e-beam being scanned over a portion of a target, the beam shape and energy characteristics of source x-ray beam 650-1 can be quickly changed when the angle of incidence between x-ray beam 660-1 and thin film 141 is changed. This adjustment can be made to improve the characteristics of the resulting output x-ray beam 670-1.

Figure 7A:
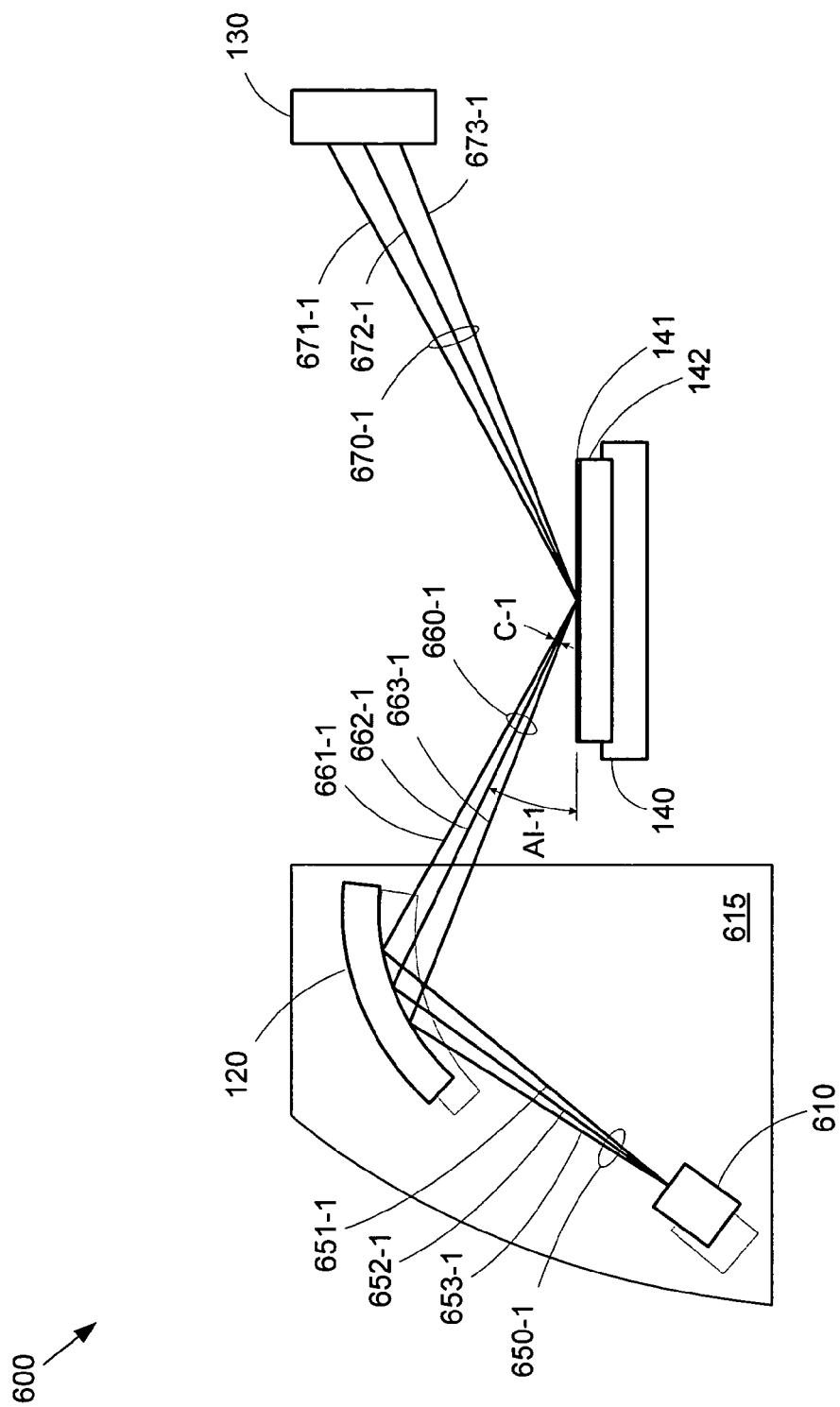
FIG. 7A shows an exemplary method of operating the x-ray reflectometry system of FIG. 6A to enable reflectometry measurements to be taken across multiple angles of incidence.
Figure 7B:
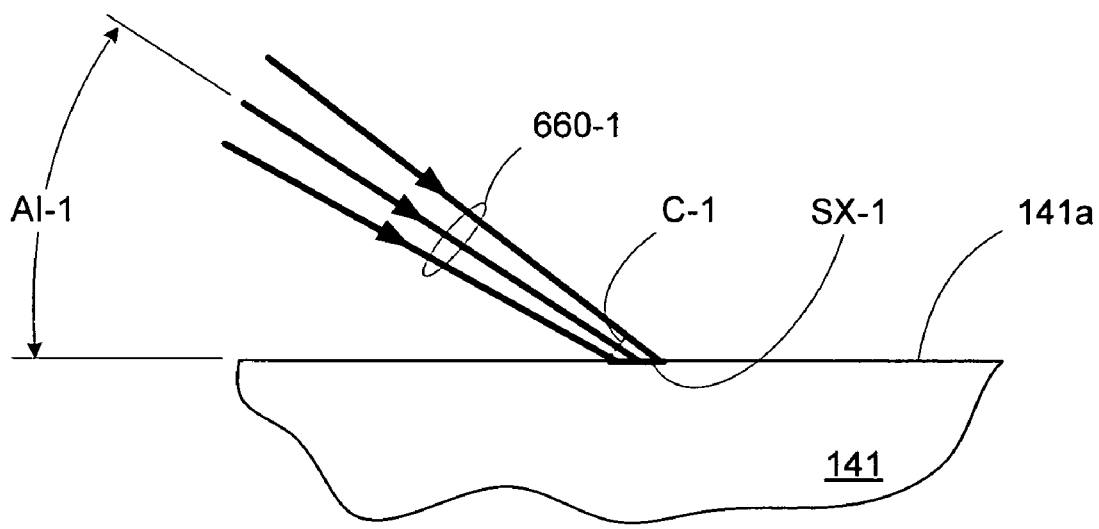
FIGS. 7B and 7C show exemplary details of x-ray beam spreading in the x-ray reflectometry system of FIG. 7A.
Figure 7C:
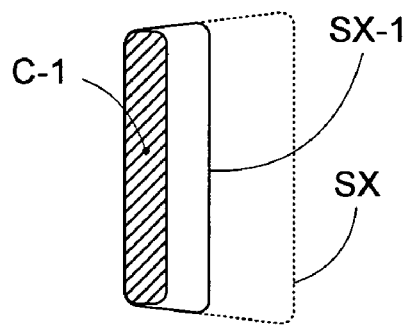

For example, FIG. 7B shows a detail view of x-ray beam 660-1 striking thin film layer 141 is shown in FIG. 7A. X-ray beam 660-1 is focused to a minimum x-ray beam cross-section C-1, and forms an illuminated spot SX-1 where thin film surface 141a intersects x-ray beam 660-1. Note that while the area of illuminated spot SX-1 is still greater than cross-section C-1 due to spreading at thin film surface 141a, the difference between the two is reduced compared to that shown in FIG. 6B due to the increased angle of incidence AI-1. This increased similarity between beam cross-section C-1 and illuminated spot SX-1 is shown in greater detail in FIG. 7C (with the outline of illuminated spot SX from FIG. 6B shown as a dotted line for reference).

Because x-ray tube 610 can quickly change the shape of the source region on the target from which the source x-ray beam is generated (by adjusting the scanning pattern of the e-beam within x-ray tube 610), reflectometry system 600 can easily and conveniently adjust the shape of the illuminated spot (SX) formed on thin film layer 141. This ease of adjustment also allows the x-ray flux to be adjusted for different angles of incidence. For example, a larger angle of incidence between x-ray beam 660 and thin film layer 141 produces an illuminated spot on the wafer that is smaller than the illuminated spot that is obtained at lower angles of incidence. This large incident angle illuminated spot may therefore be smaller than is necessary. Accordingly, in one embodiment, the illuminated spots for larger angles of incidence can be increased in size to match the sizes of the illuminated spots obtained at lower angles of incidence. This size increase can be achieved by a corresponding increase in the size of the x-ray source spot on the target within x-ray tube 610 (e.g., by increasing source spot 521 in FIG. 5A).

Note that when the source spot size on an e-beam target is increased, the thermal power density deposited into that target is decreased because even though the total power of the e-beam has not changed, the area exposed by the e-beam has increased. This decreased thermal power density does not maximize efficiency, since more thermal power can be removed from the target now that the area of the source spot has increased. To maximize efficiency, the total thermal power, and therefore the total e-beam power can be increased as the source spot area is increased. This will have the effect of increasing the total x-ray flux in the x-ray beam (650) emitted by the x-ray tube (610). Thus, as the angle of incidence is increased, the area of the x-ray source spot can be increased, the e-beam power can be increased, and the total incident x-ray flux can be increased, all without increasing the illuminated spot area on the sample.

Increasing total x-ray flux at higher angles of incidence is typically very beneficial because the reflectivity of a test sample (e.g., test sample 140) and the total x-ray signal (e.g., of reflected x-ray beam 670) at the detector (e.g., detector 630) decreases at higher angles of incidence (as indicated by the graph in FIG. 2). The increase in total x-ray flux at higher angles of incidence can partially compensate for this effect, thereby providing a higher signal to noise ratio than is otherwise possible at the higher incidence angles.

Thus, the power of the e-beam used within x-ray tube 610 to generate source x-ray beam 650 can be increased when measurements are being taken at larger angles of incidence. In one embodiment, x-ray tube 610 can include one or more control grids between the electron source (510 in FIG. 5A) and the target (520). The target (anode) can then be maintained at a fixed high voltage (e.g., 10–70 keV) while the voltage on the control grid(s) is varied to change the e-beam current (energy). Various other e-beam energy adjustment systems will be readily apparent. By increasing the flux of source x-ray beam 650, the flux of the x-rays in output x-ray beam 670 can be increased to compensate for the reduced reflectivity at larger angles of incidence.

For example, in FIG. 6A, x-ray beam 660 forms an angle of incidence AI equal to 0.750 with thin film layer 141, x-ray tube 610 can be configured to generate source x-ray beam 650 from a 1 μm×40 μm source region on the target (such as described with respect to FIG. 5D) exposed by an e-beam at voltage 25 keV and current 1 mA. Then, when the angle of incidence is increased to 1.250 in FIG. 7A, x-ray tube 610 can adjust the scanning pattern of the e-beam to expose a 2 μm×40 μm source region on the target, and can increase the e-beam energy by increasing the e-beam current to 2 mA. In this manner, the illuminated spot for both angles of incidence can be maintained at roughly the same size, while the inherently reduced output signal strength at the larger angle of incidence can be compensated for by the increased energy of source x-ray beam 660-1 generated by x-ray tube 610. Note that in various embodiments, x-ray tube 610 can be configured to automatically adjust the x-ray source spot (e.g., 521) shape and/or the e-beam (e.g., 512) power depending on the position of x-ray tube 610 and/or x-ray reflector 120 (e.g., based on data from position adjustment mechanism 615).

FIG. 8A shows an x-ray reflectometry system 800A in accordance with another embodiment of the present invention. X-ray reflectometry system 800A is substantially similar to x-ray reflectometry system 600 shown in FIG. 6A, except that in addition to an x-ray tube 810, an x-ray reflector 820, a detector 830, and a stage 840, reflectometry system 800A includes an angle-limiting gate 881. X-ray tube 810 is configured to generate a source x-ray beam 850 by scanning an e-beam across a source region of an x-ray target and can be substantially similar to x-ray tube 500 described with respect to FIG. 5A. X-ray reflector 820 reflects and focuses source x-ray beam 850 into a converging x-ray beam 860 directed at a thin film layer 841 on a test sample 842. Test sample 842 is held in place by stage 840. Converging x-ray beam 860 is then reflected by thin film layer 841 onto detector 830 as an output x-ray beam 870. According to an embodiment of the present invention, x-ray reflector 820 comprises a monochromator. According to another embodiment of the present invention, x-ray tube 810 generates an x-ray beam from a source region on a target having a non-unitary aspect ratio, the long dimension of the emitting being substantially perpendicular to the direction of source x-ray beam 850.

Angle limiting gate 881 is opaque to x-rays and can be positioned to prevent a portion of the x-rays emitted by x-ray tube 810 from reaching thin film layer 841. According to an embodiment of the present invention, angle-limiting gate 881 is configured to block only those x-rays in x-ray beam 860 forming a relative angle with thin film surface 841a less than a threshold angle At. For example, source x-ray beam 850 includes individual x-rays 851–855, which correspond to x-rays 861–865, respectively, in focused x-ray beam 860. X-rays 861–863, which form relative angles with thin film surface 841a that are greater than threshold angle At, are not affected by angle limiting gate 881 and are reflected as x-rays 871–873, respectively, in output x-ray beam 870. However, x-rays 864 and 865, which form relative angles with thin film surface 841a that are less than threshold angle At, are blocked by angle limiting gate 881. Therefore, x-rays 864 and 865 never reach thin film layer 841 and so cannot scatter to contaminate the measurements of x-rays 871–873 by sensor 830.

According to another embodiment of the present invention, angle-limiting gate could be replaced by an angle-limiting gate 883 (indicated by a dotted outline). Rather then being positioned between x-ray reflector 820 and stage 840, angle-limiting gate 883 could be placed between x-ray tube 810 and x-ray reflector 820. Angle-limiting gate 883 would then block those x-rays in source x-ray beam 850 corresponding to those x-rays in focused x-ray beam 860 forming a relative angle with thin film surface 841 less than threshold angle At.

Figure 8B:
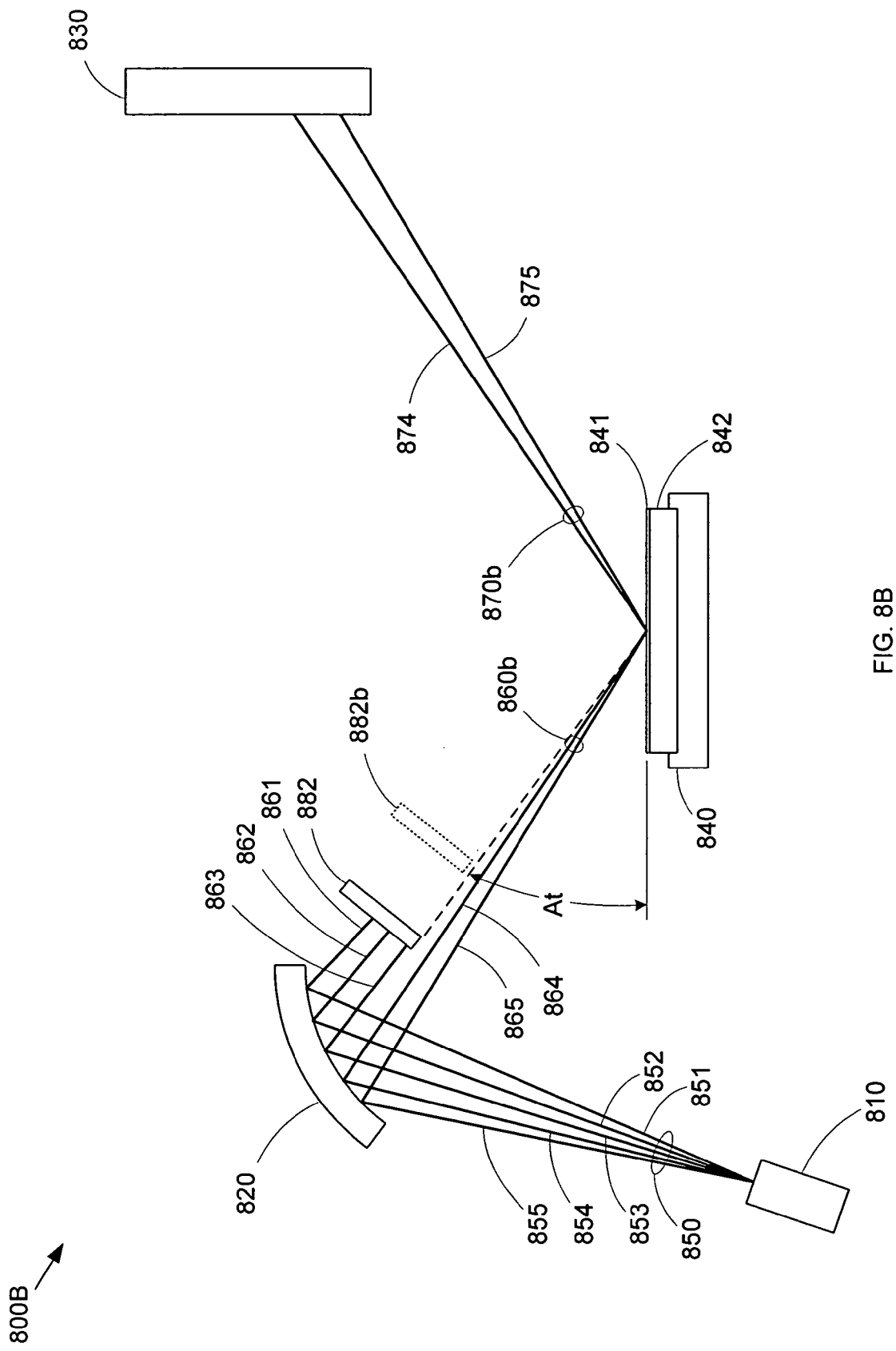

FIG. 8B shows an x-ray reflectometry system 800B in accordance with another embodiment of the present invention. X-ray reflectometry system 800B is substantially similar to x-ray reflectometry system 800A shown in FIG. 8A, except that angle limiting gate 881 is replaced with an angle limiting gate 882. Rather than blocking x-rays below threshold angle At, angle limiting gate 882 blocks those x-rays forming relative angles with thin film surface 841 greater than threshold angle At. Therefore, x-rays 864 and 865 are passed by angle limiting gate 881 and are reflected as x-rays 874 and 875, respectively, while x-rays 864 and 865, which form relative angles with thin film surface 841a that are less than threshold angle At, are blocked. Therefore, measurements of x-rays 874 and 875 by sensor 830 are not contaminated by scattering from x-rays 861–863.

According to an embodiment of the present invention, x-ray reflectometry system 800A shown in FIG. 8A could be used in conjunction with x-ray reflectometry system 800B, thereby facilitating measurement across the full range of x-rays in source x-ray beam 850. A measurement with only angle-limiting gate 881 in place could be performed, followed by a measurement with only angle-limiting gate 882 in place. The results of the two measurements could be combined to obtain the complete reflectivity curve. According to another embodiment of the present invention, angle-limiting gates 881 and 882 shown in FIGS. 800A and 800B, respectively, could represent two positions of a single movable angle-limiting gate.

According to another embodiment of the present invention, angle-limiting gate 882 of x-ray reflectometry system 800B could be removable, in which case two measurements could be taken—one with angle-limiting gate 882 in place, and one with angle-limiting gate 882 removed. Scattering effects detected in the gated first measurement could then be subtracted from the results of the non-gated measurement. X-ray reflectometry system 800A could be operated in a similar manner.

Figure 8C:
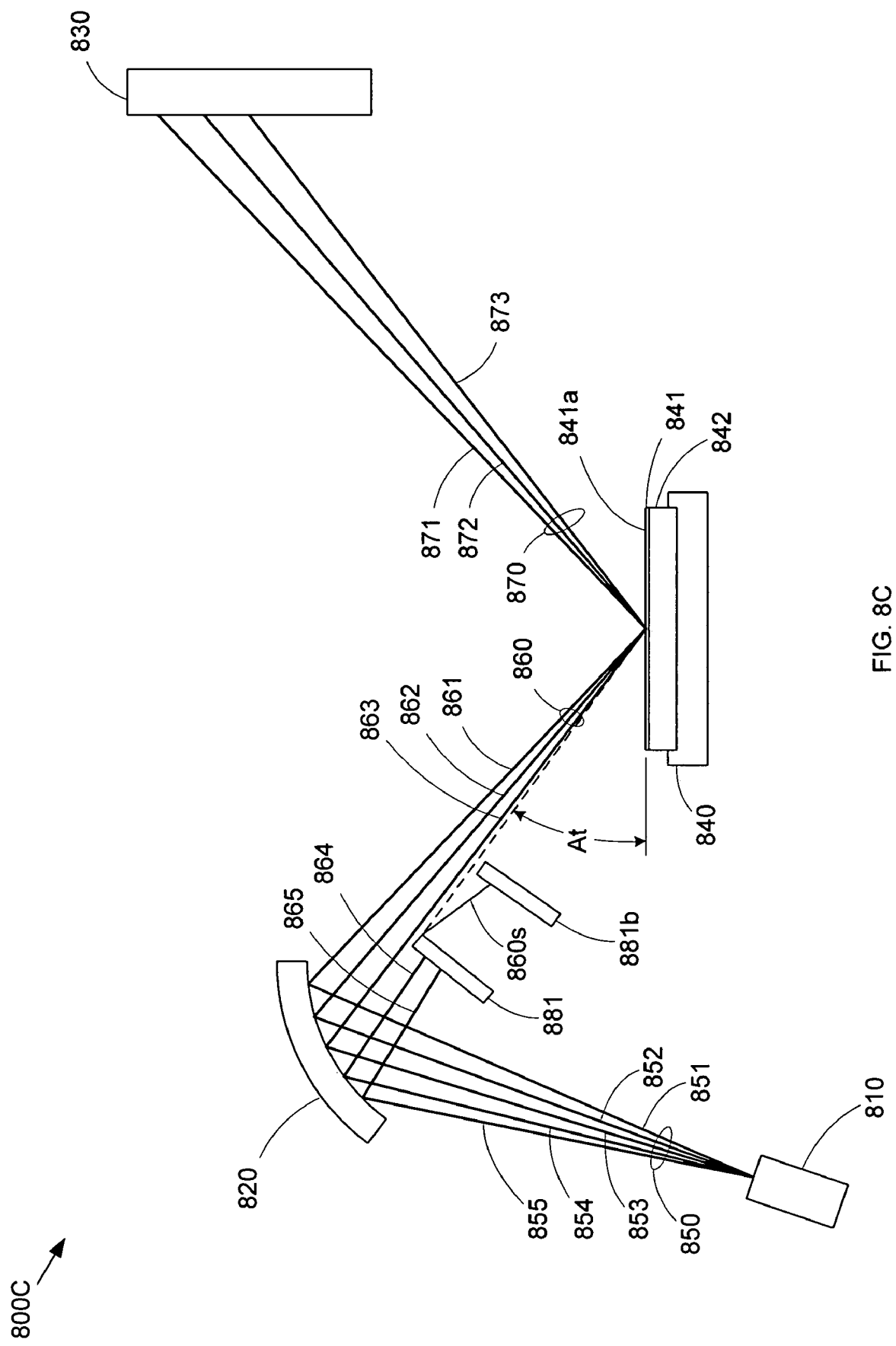

FIG. 8C shows an x-ray reflectometry system 800C in accordance with another embodiment of the present invention. X-ray reflectometry system 800C includes a secondary guard gate 881b between angle limiting gate 881 and test sample 842. In other respects, x-ray reflectometry system 800C is substantially similar to x-ray reflectometry system 800A shown in FIG. 8A. Secondary guard gate 881b is aligned in the beam direction with angle limiting gate 881, but positioned slightly below the beam horizon, i.e., the edge of secondary guard gate 881b is positioned so as to be just below the x-rays passed by angle-limiting gate 881. Therefore, secondary guard gate does not affect the x-rays above threshold angle At, but can block any x-rays scattered from the edge of angle-limiting gate 881, such as x-ray 860s. In this manner, secondary guard gate further enhances the accuracy of the measurements taken by detector 830. A similar secondary guard gate 882b (indicated by a dotted outline) could be added to x-ray reflectometry system 800B shown in FIG. 8B, to block scattering from the edge of angle-limiting gate 882.

Figure 8D:
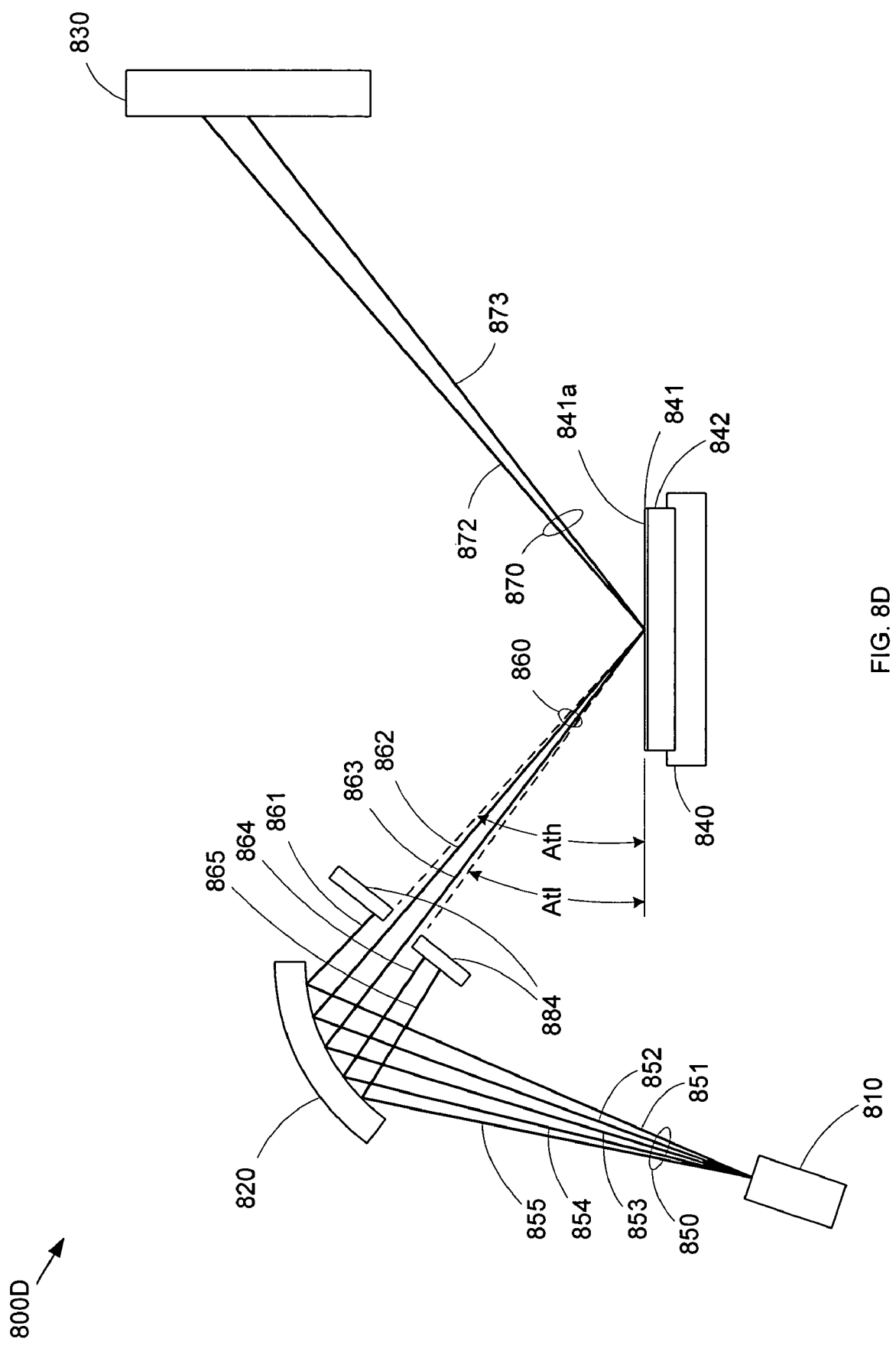

FIG. 8D shows an x-ray reflectometry system 800D in accordance with another embodiment of the present invention. X-ray reflectometry 800D is substantially similar to x-ray reflectometry system 800A shown in FIG. 8A, except that angle-limiting gate 881 of x-ray reflectometry system 800A is replaced with a slotted gate 884 in x-ray reflectometry system 800D. Only those x-rays forming relative angles with thin film surface 841a between a lower threshold angle At1 and an upper threshold angle Ath are passed by slotted gate 884 to thin film layer 841. By adjusting the position of slotted gate 884 with respect to x-ray reflector 820, a series of reflectivity measurements can be taken. The individual measurements can then be combined to form a complete reflectivity curve.

Although the present invention has been described in connection with several embodiments, it is understood that this invention is not limited to the embodiments disclosed, but is capable of various modifications that would be apparent to one of ordinary skill in the art. Thus, the invention is limited only by the following claims.

I claim:

1. An x-ray reflectometry system for performing reflectometry on a test sample, the x-ray reflectometry system comprising:
   an x-ray tube for generating an x-ray beam;
   beam focusing optics for focusing the x-ray beam onto a measurement location on the test sample; and
   a sensor for measuring x-rays reflected from the test sample,
   wherein the x-ray tube comprises:
      a target;
      an electron source for generating an electron beam; and
      a scanning mechanism for scanning the electron beam across a source region of the target to cause the source region to emit the x-ray beam, wherein the source region is larger than a cross-section of the electron beam.

2. The x-ray reflectometry system of claim 1, wherein the source region has a non-unitary aspect ratio, and
   wherein a long dimension of the source region is positioned substantially perpendicular to a direction of the x-ray beam.

3. The x-ray reflectometry system of claim 1, wherein the scanning mechanism comprises a beam deflection element.

4. The x-ray reflectometry system of claim 1, wherein the scanning mechanism comprises a positioning mechanism for adjusting a relative position between the electron source and the target.

5. The x-ray reflectometry system of claim 1, wherein the x-ray tube further comprises a beam shaping element for adjusting a cross-sectional shape of the electron beam before the electron beam is scanned across the source region of the target.

6. The x-ray reflectometry system of claim 1, wherein the sensor comprises a sensor array for measuring intensities of the x-rays reflected from the test sample over a plurality of measurement locations on the sensor array.

7. The x-ray reflectometry system of claim 6, wherein the x-ray beam consists of a plurality of source x-rays,
   a first gate for blocking a first group of the plurality of source x-rays without impeding a second group of the plurality of source x-rays, the second group of the plurality of source x-rays forming a plurality of incident angles with the measurement location.

8. The x-ray reflectometry system of claim 7, further comprising a second gate for blocking x-rays scattered by the first gate without impeding the second group of the plurality of x-rays.

9. The x-ray reflectometry system of claim 1, further comprising a positional adjustment mechanism for adjusting an angle of incidence between the x-ray beam and the measurement location.

10. The x-ray reflectometry system of claim 9, wherein the positional adjustment mechanism comprises a goniometer.

11. The x-ray reflectometry system of claim 9, wherein the x-ray tube and focusing optic generate the x-ray beam with a narrow cone.

12. The x-ray reflectometry system of claim 9, wherein the sensor comprises a single element detector for measuring a total intensity of the x-rays reflected from the test sample.

13. The x-ray reflectometry system of claim 9, wherein the x-ray source spot area is set to automatically change with the position of the x-ray source and x-ray focusing optic.

14. The x-ray reflectometry system of claim 9, wherein the e-beam power is set to automatically change with the position of the x-ray source and x-ray focusing optic.

15. A method for taking an x-ray reflectometry measurement, the method comprising:
   generating a first x-ray beam by scanning a first electron beam across a first source region of a target to cause the first source region to emit the first x-ray beam;
   focusing the first x-ray beam onto a measurement location on a test sample; and
   measuring a first set of x-rays reflected from the measurement location.

16. The method of claim 15, wherein the first source region has a non-unitary aspect ratio, and
   wherein a long dimension of the first source region is substantially perpendicular to a direction of the first x-ray beam.

17. The method of claim 15, wherein measuring the first set of x-rays reflected from the measurement location comprises:
   measuring an intensity at each of a set of detection locations on a sensor array; and
   correlating the intensity at each of the set of detection locations with an angle of incidence to generate a reflectivity curve.

18. The method of claim 15, further comprising:
   generating a second x-ray beam by scanning a second electron beam across a second source region of the target to cause the second source region to emit the second x-ray beam;
   focusing the second x-ray beam onto the measurement location on the test sample; and
   measuring a second set of x-rays reflected from the measurement location.

19. The method of claim 18, wherein the second source region has a different shape than the first source region.

20. The method of claim 19, wherein measuring the first set of x-rays reflected from the measurement location comprises measuring a first total intensity of the first set of x-rays and correlating the first total intensity with a first angle of incidence between the first x-ray beam and the measurement location, and
   wherein measuring the second set of x-rays reflected from the measurement location comprises measuring a second total intensity of the second set of x-rays and correlating the second total intensity with a second angle of incidence between the second x-ray beam and the measurement location.

21. The method of claim 20, wherein the second angle of incidence is greater than the first angle of incidence, and
   wherein a power of the second electron beam is greater than a power of the first electron beam.

* * * * *